(12) United States Patent
Wang et al.

(10) Patent No.: US 11,566,045 B2
(45) Date of Patent: Jan. 31, 2023

(54) TUMOR TARGETING POLYPEPTIDE AND METHOD OF USE THEREOF

(71) Applicant: Zhejiang Reachall Pharmaceutical Co. Ltd., Dongyang (CN)

(72) Inventors: Fujun Wang, Dongyang (CN); Jian Zhao, Shanghai (CN); Xuewei Cao, Shanghai (CN); Longyun Fu, Dongyang (CN); Taozhu Zhang, Dongyang (CN); Hanwen Shan, Dongyang (CN); Xuzhong Yang, Dongyang (CN)

(73) Assignee: Zhejiang FONOW Medicine Co., Ltd, Dongyang (CN)

( * ) Notice: Subject to any disclaimer, the term of this patent is extended or adjusted under 35 U.S.C. 154(b) by 0 days.

(21) Appl. No.: 15/562,722

(22) PCT Filed: Mar. 14, 2017

(86) PCT No.: PCT/CN2017/076656
§ 371 (c)(1),
(2) Date: Oct. 29, 2019

(87) PCT Pub. No.: WO2018/165867
PCT Pub. Date: Sep. 20, 2018

(65) Prior Publication Data
US 2022/0153781 A1    May 19, 2022

(51) Int. Cl.
| | | |
|---|---|---|
| *C07K 7/06* | (2006.01) | |
| *A61P 35/00* | (2006.01) | |
| *A61K 45/06* | (2006.01) | |
| *A61K 47/42* | (2017.01) | |
| *A61K 38/00* | (2006.01) | |

(52) U.S. Cl.
CPC ............... *C07K 7/06* (2013.01); *A61K 45/06* (2013.01); *A61K 47/42* (2013.01); *A61P 35/00* (2018.01); *A61K 38/00* (2013.01)

(58) Field of Classification Search
CPC ........ A61K 38/00; A61K 45/00; A61K 45/06; A61K 47/42; A61K 49/00; A61K 9/0019; A61P 35/00; C07K 14/00; C07K 2319/10; C07K 7/06
See application file for complete search history.

(56) References Cited

U.S. PATENT DOCUMENTS

| | | | | |
|---|---|---|---|---|
| 6,057,155 A * | 5/2000 | Wickham | ................ | C12N 15/86 536/23.4 |
| 8,715,986 B2 * | 5/2014 | Gonzalez | ................ | A61P 25/28 530/402 |
| 2015/0182596 A1 * | 7/2015 | Lee | ........................ | A61K 38/29 435/320.1 |

FOREIGN PATENT DOCUMENTS

CN    104140457 A    11/2014

OTHER PUBLICATIONS

Nomizu et al. Multimeric Forms of Tyr-Ile-Gly-Ser-Arg (YIGSR) Peptide Enhance the Inhibition of Tumor Growth and Metastasis. Cancer Research, vol. 53, Issue 15, pp. 3459-3461. (Year: 1993).*
Capela et al. Analysis of the chromosome sequence of the legume symbiont Sinorhizobium meliloti strain 1021. PNAS, vol. 98, No. 17, pp. 9877-9882. (Year: 2001).*
Dixon et al. Highly efficient delivery of functional cargoes by the synergistic effect of GAG binding motifs and cell-penetrating peptides. PNAS, E291-E299. (Year: 2016).*
Luo et al. The heparin-binding domain of HB-EGF as an efficient cell-penetrating peptide for drug delivery J. Pept. Sci. 2016; vol. 22: pp. 689-699. (Year: 2016).*
Yarden Y, Sliwkowski MX. Untangling the ErbB signalling network. Nat Rev Mol Cell Biol 2001;2:127e37.
Herbst RS, Shin DM. Monoclonal antibodies to target epidermal growth factor receptor-positive tumors: a new paradigm for cancer therapy. Cancer 2002;94:1593e611.
Yewale C, Baradia D, Vhora I, Patil S, Misra A. Epidermal growth factor receptor targeting in cancer: a review of trends and strategies. Biomaterials 2013;34(34):8690-707.
Prigent SA, Lemoine NR. The type 1 (EGFR-related) family of growth factor receptors and their ligands. Prog Growth Factor Res. 1992;4(1):1-24.
Ogiso H, Ishitani R, Nureki O, Fukai S, Yamanaka M, Kim JH, Saito K, Sakamoto A, Inoue M, Shirouzu M, Yokoyama S. Crystal structure of the complex of human epidermal growth factor and receptor extracellular domains. Cell. 2002 ;110(6):775-87.
Nestor JJ Jr, Newman SR, DeLustro B, Todaro GJ, Schreiber AB. A synthetic fragment of rat transforming growth factor alpha with receptor binding and antigenic properties Biochem Biophys Res Commun. 1985;129(1):226-32.
Lin YZ, Ke XH, Tam JP. Growth inhibition by vaccinia virus growth factor. J Biol Chem. 1990;265(31):18884-90.
Ding Y, Tan W, Hu R, Chen W, Hou Y. Construction of a novel fusion protein harboring mouse interferon gamma and epidermal growth factor receptor binding domain and enhancement of its antitumor activity. Sci China C Life Sci. 1997;40(3):293-300.
Lelle M, Kaloyanova S, Freide C, Theodoropoulou M, Musheev M, Niehrs C, Stalla G, Peneva K. Octreotide-Mediated Tumor-Targeted Drug Delivery via a Cleavable Doxorubicin-Peptide Conjugate. Mol Pharm. 2015;12(12):4290-300.
Eppstein DA, Marsh YV, Schryver BB, Berties PJ. Inhibition of epidermal growth factor/transforming growth factor-alpha-stimulated cell growth by a synthetic peptide. J Cell Physiol. 1989;141(2):420-30.

(Continued)

*Primary Examiner* — Marcela M Cordero Garcia
(74) *Attorney, Agent, or Firm* — Zhihua Han

(57) ABSTRACT

The application relates to the field of biopharmaceuticals, in particular to tumor-targeting peptides and method for preparation and application thereof. The application discloses a tumor-targeting peptide. The tumor-target peptide displays better binding specificity and capability, thereby alleviates the effect of cancer treatment drugs on normal cells, reduces the incidence of adverse drug reactions, and improves the therapeutic effect.

19 Claims, 8 Drawing Sheets

Specification includes a Sequence Listing.

(56) References Cited

OTHER PUBLICATIONS

Overholser J, Ambegaokar KH, Eze SM, Sanabria-Figueroa E, Nahta R, Bekaii-Saab T, Kaumaya PT. Anti-Tumor Effects of Peptide Therapeutic and Peptide Vaccine Antibody Co-targeting HER-1 and HER-2 in Esophageal Cancer (EC) and HER-1 and IGF-1R in Triple-Negative Breast Cancer (TNBC). Vaccines (Basel). 2015;3(3):519-43.

Li F, Cheng T, Dong Q, Wei R, Zhang Z, Luo D, Ma X, Wang S, Gao Q, Ma D, Zhu X, Xi L. Evaluation of (99m)Tc-HYNIC-TMTP1 as a tumor-homing imaging agent targeting metastasis with SPECT. Nucl Med Biol. 2015;42(3):256-62.

Hyvönen M, Enbäck J, Huhtala T, Lammi J, Sihto H, Weisell J, Joensuu H, Rosenthal-Aizman K, El-Andaloussi S, Langel U, Närvänen A, Bergers G, Laakkonen P. Novel target for peptide-based imaging and treatment of brain tumors. Mol Cancer Ther. 2014;13(4):996-1007.

Han C, Li Y, Sun M, Liu C, Ma X, Yang X, Yuan Y, Pan W. Small peptide-modified nanostructured lipid carriers distribution and targeting to EGFR-overexpressing tumor in vivo. Artif Cells Nanomed Biotechnol. 2014;42(3):161-6.

Zhu S, Zhang J, Janjanam J, Bi J, Vegesna G, Tiwari A, Luo FT, Wei J, Liu H. Highly water-soluble, near-infrared emissive BODIPY polymeric dye bearing RGD peptide residues for cancer imaging. Anal Chim Acta. 2013;758:138-44.

Jie LY, Cai LL, Wang LJ, Ying XY, Yu RS, Zhang MM, Du YZ. Actively-targeted LTVSPWY peptide-modified magnetic nanoparticles for tumor imaging. Int J Nanomedicine. 2012;7:3981-9.

He X, Na MH, Kim JS, Lee GY, Park JY, Hoffman AS, Nam JO, Han SE, Sim GY, Oh YK, Kim IS, Lee Bh. A novel peptide probe for imaging and targeted delivery of liposomal doxorubicin to lung tumor Mol Pharm. 2011;8(2):430-8.

\* cited by examiner

SEQUENCE LISTING

```
<160> NUMBER OF SEQ ID NOS: 23

<210> SEQ ID NO 1
<211> LENGTH: 31
<212> TYPE: PRT
<213> ORGANISM: Artificial Sequence
<220> FEATURE:
<223> OTHER INFORMATION: synthesized

<400> SEQUENCE: 1

Arg Cys Ser His Tyr Thr Gly Ile Arg Cys Ser His Met Ala Ala Thr
1               5                   10                  15

Thr Ala Gly Ile Tyr Thr Gly Ile Arg Cys Gln His Val Val Leu
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: synthesized

<400> SEQUENCE: 2

Arg Ala Ser His Tyr Thr Gly Ile Arg Cys Ser His Met Ala Ala Thr
1               5                   10                  15

Thr Ala Gly Ile Tyr Thr Gly Ile Arg Cys Gln His Val Val Leu
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: synthesized

<400> SEQUENCE: 3

Arg Cys Ser His Tyr Thr Gly Ile Arg Ala Ser His Met Ala Ala Thr
1               5                   10                  15
```

Thr Ala Gly Ile Tyr Thr Gly Ile Arg Cys Gln His Val Val Leu
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: synthesized

<400> SEQUENCE: 4

Arg Cys Ser His Tyr Thr Gly Ile Arg Cys Ser His Met Ala Ala Thr
1               5                   10                  15

Thr Ala Gly Ile Tyr Thr Gly Ile Arg Gly Gln His Val Val Leu
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: synthesized

<400> SEQUENCE: 5

Arg Cys Ser His Tyr Thr Gly Ile Arg Cys Ser Glu Ala Ala Ala Lys
1               5                   10                  15

Glu Ala Gly Ile Tyr Thr Gly Ile Arg Cys Gln His Val Val Leu
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: synthesized

<400> SEQUENCE: 6

Arg Cys Ser His Tyr Thr Gly Ile Arg Cys Ser Gly Gly Gly Gly Ser
1               5                   10                  15

Gly Ala Gly Ile Tyr Thr Gly Ile Arg Cys Gln His Val Val Leu
            20                  25                  30

<210> SEQ ID NO 7
<211> LENGTH: 23
<212> TYPE: PRT
<213> ORGANISM: Artificial Sequence
<220> FEATURE:
<223> OTHER INFORMATION: synthesized

<400> SEQUENCE: 7

Arg Cys Ser His Met Ala Ala Thr Thr Ala Gly Ile Tyr Thr Gly Ile
1               5                   10                  15

Arg Cys Gln His Val Val Leu
            20

<210> SEQ ID NO 8
<211> LENGTH: 28
<212> TYPE: PRT
<213> ORGANISM: Artificial Sequence
<220> FEATURE:
<223> OTHER INFORMATION: synthesized

<400> SEQUENCE: 8

Arg Cys Ser Tyr Thr Gly Ile Arg Cys Ser His Met Ala Ala Thr
1               5                   10                  15

Thr Ala Gly Ile Tyr Thr Gly Ile Arg Cys Gln His
            20                  25

<210> SEQ ID NO 9
<211> LENGTH: 25
<212> TYPE: PRT
<213> ORGANISM: Artificial Sequence
<220> FEATURE:
<223> OTHER INFORMATION: synthesized

<400> SEQUENCE: 9

Arg Cys Ser His Tyr Thr Gly Ile Arg Cys Ser His Gly Ile Tyr Thr
1               5                   10                  15

Gly Ile Arg Cys Gln His Val Val Leu
            20                  25

<210> SEQ ID NO 10
<211> LENGTH: 27
<212> TYPE: PRT
<213> ORGANISM: Artificial Sequence
<220> FEATURE:
<223> OTHER INFORMATION: synthesized

<400> SEQUENCE: 10

Tyr Thr Gly Ile Arg Cys Ser His Met Ala Ala Thr Thr Ala Gly Ile
1               5                   10                  15

Tyr Thr Gly Ile Arg Cys Gln His Val Val Leu
            20                  25

<210> SEQ ID NO 11
<211> LENGTH: 31
<212> TYPE: PRT
<213> ORGANISM: Artificial Sequence
<220> FEATURE:
<223> OTHER INFORMATION: synthesized

<400> SEQUENCE: 11

Arg Cys Ser His Tyr Thr Gly Ile Arg Cys Ser His Gly Ala Ala Ala
1               5                   10                  15

Ala Ala Gly Ile Tyr Thr Gly Ile Arg Cys Gln His Val Val Leu
            20                  25                  30

<210> SEQ ID NO 12
<211> LENGTH: 21
<212> TYPE: PRT
<213> ORGANISM: Artificial Sequence
<220> FEATURE:
<223> OTHER INFORMATION: synthesized

<400> SEQUENCE: 12

Lys Arg Lys Lys Lys Gly Lys Gly Leu Gly Lys Lys Arg Asp Pro Cys
1               5                   10                  15

Leu Arg Lys Tyr Lys
            20

<210> SEQ ID NO 13
<211> LENGTH: 56
<212> TYPE: PRT
<213> ORGANISM: Artificial Sequence
<220> FEATURE:
<223> OTHER INFORMATION: synthesized

<400> SEQUENCE: 13

Arg Cys Ser His Tyr Thr Gly Ile Arg Cys Ser His Met Ala Ala Thr
1               5                   10                  15

Thr Ala Gly Ile Tyr Thr Gly Ile Arg Cys Gln His Val Val Leu Val
                20                  25                  30

Asp Gly Gly Lys Arg Lys Lys Gly Lys Gly Leu Gly Lys Lys Arg
            35                  40                  45

Asp Pro Cys Leu Arg Lys Tyr Lys
    50                  55

<210> SEQ ID NO 14
<211> LENGTH: 53
<212> TYPE: PRT
<213> ORGANISM: Artificial Sequence
<220> FEATURE:
<223> OTHER INFORMATION: synthesized

<400> SEQUENCE: 14

Arg Cys Ser His Tyr Thr Gly Ile Arg Cys Ser His Met Ala Ala Thr
1               5                   10                  15

Thr Ala Gly Ile Tyr Thr Gly Ile Arg Cys Gln His Val Asp Gly Gly
                20                  25                  30

Lys Arg Lys Lys Gly Lys Gly Leu Gly Lys Lys Arg Asp Pro Cys
            35                  40                  45

Leu Arg Lys Tyr Lys
    50

<210> SEQ ID NO 15
<211> LENGTH: 50
<212> TYPE: PRT
<213> ORGANISM: Artificial Sequence
<220> FEATURE:
<223> OTHER INFORMATION: synthesized

<400> SEQUENCE: 15

Arg Cys Ser His Tyr Thr Gly Ile Arg Cys Ser His Gly Ile Tyr Thr
1               5                   10                  15

Gly Ile Arg Cys Gln His Val Val Leu Val Asp Gly Gly Lys Arg Lys
                20                  25                  30

Lys Lys Gly Lys Gly Leu Gly Lys Lys Arg Asp Pro Cys Leu Arg Lys
            35                  40                  45

Tyr Lys
    50

<210> SEQ ID NO 16
<211> LENGTH: 16
<212> TYPE: PRT
<213> ORGANISM: Artificial Sequence
<220> FEATURE:
<223> OTHER INFORMATION: synthesized

<400> SEQUENCE: 16

Arg Cys Ser His Gly Tyr Thr Gly Ile Arg Cys Gln His Val Val Leu
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: synthesized

<400> SEQUENCE: 17

Arg Cys Ser His Gly Tyr Thr Gly Ile Arg Cys Gln Ala Val Val Leu
1               5                   10                  15

<210> SEQ ID NO 18
<211> LENGTH: 37
<212> TYPE: DNA
<213> ORGANISM: Artificial Sequence
<220> FEATURE:
<223> OTHER INFORMATION: synthesized

<400> SEQUENCE: 18
cgcggatccg gtggtggtgg ttctggtggt ggtggtt                                37

<210> SEQ ID NO 19
<211> LENGTH: 21
<212> TYPE: DNA
<213> ORGANISM: Artificial Sequence
<220> FEATURE:
<223> OTHER INFORMATION: synthesized

<400> SEQUENCE: 19
cgcctcgagg tctttacctt t                                                 21

<210> SEQ ID NO 20
<211> LENGTH: 6
<212> TYPE: PRT
<213> ORGANISM: Artificial Sequence
<220> FEATURE:
<223> OTHER INFORMATION: synthesized

<400> SEQUENCE: 20

His Met Ala Ala Thr Thr
1               5

<210> SEQ ID NO 21
<211> LENGTH: 12
<212> TYPE: PRT
<213> ORGANISM: Artificial Sequence
<220> FEATURE:
<223> OTHER INFORMATION: synthesized

<400> SEQUENCE: 21

Tyr Gly Arg Lys Lys Arg Arg Arg Arg Arg Arg Arg
1               5                   10

<210> SEQ ID NO 22
<211> LENGTH: 27
<212> TYPE: PRT
<213> ORGANISM: Artificial Sequence
<220> FEATURE:
<223> OTHER INFORMATION: synthesized

<400> SEQUENCE: 22

Gly Pro Gly Leu Trp Glu Arg Gln Ala Arg Glu His Ser Glu Arg Lys
1               5                   10                  15

Lys Arg Arg Arg Glu Ser Glu Cys Lys Ala Ala
            20                  25

<210> SEQ ID NO 23
<211> LENGTH: 5
<212> TYPE: PRT
<213> ORGANISM: Artificial Sequence
<220> FEATURE:
<223> OTHER INFORMATION: synthesized

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 23

Tyr Xaa Gly Xaa Arg
1               5
```

TUMOR TARGETING POLYPEPTIDE AND METHOD OF USE THEREOF

CROSS REFERENCE TO RELATED APPLICATION

This application claims the priority and benefit of PCT Application No. PCT/CN2017/076656 filed Mar. 4, 2017, which is hereby incorporated by reference in its entirety.

SEQUENCE LISTING INFORMATION

A computer readable textfile, entitled "sequence-listing.txt," translated on or about Sep. 24, 2019 with a file size of about 8 KB, contains the sequence listing for this application and is hereby incorporated by reference in its entirety.

TECHNICAL FIELD

The application relates to the field of biopharmaceuticals, in particular to tumor-targeting peptides and method for preparation and application thereof.

BACKGROUND

Cancer is one of the three diseases that seriously affect human health and life. Of many common cancers, such as breast cancer, non-small cell lung cancer, colorectal cancer, bladder cancer, ovarian cancer, gastric cancer, pancreatic cancer, skin squamous cell carcinoma, renal cell carcinoma, head and neck cancer, and malignant glioma, epidermal growth factor receptor (EGFR) is often abnormally and overly expressed on the surface of tumor cells, and the high expression of EGFR is often associated with abnormal activity of cell proliferation. The number of EGFR on the surface of a human cell is typically in a range of $4\times10^4$ to $1\times10^5$, whereas the number of EGFR on the surface of a tumor cell may exceed $2\times10^6$ or 20-50 times of that on a normal cell. EGFR-mediated signal transduction plays an important role in tumor cell proliferation, damage repair, invasion, and angiogenesis.

The EGFR family has four members, including ErbB1/HER1/EGFR, ErbB2/HER2, ErbB3/HER3, and ErbB4/HER4, all of which can be classified as receptor tyrosine kinases. Human EGFR protein is made of 1186 amino acid residues with a relative molecular weight of 170 kD. It has three domains: 1) extracellular domain, the N-terminal 621 amino acid residues encode the ligand binding domain; 2) transmembrane domain, these 23 amino acid residues encode a helical hydrophobic structure, with which the receptor protein anchors itself in the lipid bilayer membrane of the cell; and 3) intracellular domain, these 542 amino acid residues can be further divided into 3 sub-regions: near membrane, tyrosine kinase, and carboxyl terminal, respectively.

It is known that a variety of epidermal growth factor (EGF)-like ligand molecules, also known as EGF-like ligands, can specifically bind to EGFR and exert biological effects. EGF-like ligands include EGF, Transforming Growth Factor-alpha (TGFα), Amphiregulin (AR), Betacellulin (BTC), Heparin-Binding Epidermal Growth Factor (HB-EGF), Epiregulin (EPR), and Vaccinia Virus Growth Factor (VGF).

The EGFR-binding EGF-like ligand molecules share a similar and conserved three-dimensional structure, with which each ligand molecule contains 6 cysteine residues that form three intramolecular disulfide bonds (Cys6-Cys20, Cys14-Cys31, and Cys33-Cys42, as in EGF) that result in a typical tri-loop spatial structure.

The specific recognition and binding between EGF and EGFR represent the interaction between EGF-like ligands and EGFR. EGF depends on the three structural loops to interface with EGFR, of which the C-loop specifically penetrates into the deepest structure of EGFR and plays an important role in recognition and binding.

The binding of EGF-like ligands to EGFR enables the formation of either a homodimer or a heterodimer between two EGFR molecules, which then activates the intracellular tyrosine kinase domain and phosphorylates each other's tyrosine residues. The signaling cascade leads to the transcription activation of a series of genes in the nucleus, which promotes tumor development and cell proliferation, inhibition of apoptosis, tumor cell metastasis, and tolerance to radiotherapy and chemotherapy. In analog to native EGF-like ligands, peptides may be designed and synthesized to mimic their specificity of recognition and binding. The synthetic peptides, capable of specifically recognizing and binding to EGFRs but not activating its downstream signaling cascade, can be used for transporting tumor targeting drug in vivo. Alternatively, a specific peptide may compete with EGF-like ligands for EGFR binding sites in vivo, which may inhibit tumor growth and exert certain therapeutic effects. Another application of synthetic peptides is in tumor imaging, labeling, and treatment because radiolabeled or fluorescent dye labeled peptides can enrich tumor cells after being injected into the body due to their specific binding to the surface of tumor cells. The type of peptides capable of specifically recognizing and binding to tumor cells in vitro and in vivo is called tumor-targeting peptides.

SUMMARY

The present application solves the technical problem related to a peptide structure for its ability to efficiently recognize and strongly bind to EGFRs which is overly expressed on the surface of tumor cells. Said peptides can be used for labeling, identifying, and diagnosing tumor cells, either through their binding to EGFRs or by carrying tumor targeting drugs to the surface of tumor cells and delivering targeted therapeutic effect.

In one aspect, a tumor-targeting peptide comprises a first peptide with an amino acid sequence of Y-X-G-X-R (SEQ ID NO. 23), a second peptide with an amino acid sequence of Y-X-G-X-R (SEQ ID NO. 23), and a linker peptide linking the first peptide to the second peptide, wherein Y is tyrosine or a derivative thereof, G is glycine or a derivative thereof, R is arginine or a derivative thereof, and X is an amino acid with a fatty group and/or a hydroxyl group or a combination thereof, or derivatives of amino acids.

In some embodiments, the linker peptide comprises an amino acid sequence that forms an α-helical structure, for example a structure that includes a rigid α-helix. In one embodiment, the linker peptide comprises an amino acid sequence of HMAATT (SEQ ID NO. 20).

In some embodiments, the linker peptide comprises 6 or more amino acid residues; or the linker peptide comprises less than 3 amino acid residues; or the linker peptide comprises one amino acid residue; or the linker peptide comprises histidine or its derivatives.

In some embodiments, the tumor-targeting peptide comprises a peptide having an amino acid sequence of SEQ ID NO. 1-4, SEQ ID NO. 8, SEQ ID NO. 9, or a modified derivative thereof. In one embodiment, the tumor-targeting peptide comprises a peptide having an amino acid sequence of SEQ ID NO: 1, SEQ ID NO. 8, or SEQ ID NO.9.

In some embodiments, the tumor-targeting peptide is capable of specifically binding to any member of EGFR family. In one embodiment, the tumor-targeting peptide may bind to EGFR with a kD of less than 50 nM.

In another aspect, the present application discloses a conjugate comprising a tumor-targeting peptide of one or more embodiments as described above and an active moiety that are conjugated through a linker, wherein said active moiety is a therapeutic agent, a diagnostic agent, a radio-isotope, a radionuclide, a toxin, or combinations thereof.

In some embodiments, said linker makes a connection through either a covalent or a non-covalent bond. In some embodiments, the covalent bond may be a direct covalent bond, a peptide bond, an ester bond, a disulfide bond, an amide bond, an imide bond, a phosphodiester bond, a urea bond, an isocyanate bond, or a combination thereof.

In some embodiments, said therapeutic agent comprises a cell-penetrating peptide (CPP). In one embodiment, said CPP may be a peptide with an amino acid sequence of SEQ ID NO.12, HIV transactivator protein TAT, heparin-binding domain (HBD) derived from EC-SOD, HBEGF-derived heparin-binding domain (HBD), or derivatives thereof.

In some embodiments, said conjugate comprises a peptide having an amino acid sequence of SEQ ID NO.13-15.

In some embodiments, said therapeutic agent comprises a radiotherapeutic agent, a chemotherapeutic agent, an antibody, an enzyme, or a combination thereof.

In some embodiments, said radiotherapeutic agent comprises radioisotopes, including iodine-131, lutetium-177, yttrium-90, samarium-153, phospho-32, cesium-131, palladium-223, iodine-125, boron-10, actinium-225, bismuth-213, radium-225, lead-212, thorium-232, or a combination thereof.

In some embodiments, said chemotherapeutic agent comprises capecitabine, cisplatin, trastuzumab, fulvestrant, tamoxifen, letrozole, exemestane, anastrozole, aminoglutethimide, testolactone, vorozole, formestane, Fadrozole, letrozole, erlotinib, lafatinib, dasatinib, gefitinib, imatin, Imatinib, pazopinib, lapatinib, sunitinib, nilotinib, sorafenib, nab-palitaxel, or derived from or a composition thereof.

In some embodiments, said diagnostic agent comprises a radioactive diagnostic component, a fluorescent component, a quantum dot, or a composition thereof, wherein the radiological diagnostic component comprises fluoro-18, technetium-99, molybdenum-99, rubidium-82, strontium-82, thallium-201, or a combination thereof.

In another aspect, the present application discloses the nucleic acid sequences encoding said tumor-targeting peptide.

In another aspect, the present application discloses an expression vector comprising the nucleic acid sequences encoding said tumor-targeting peptide. In one embodiment, said expression vector is intracellularly expressed.

In another aspect, the present application discloses a host cell comprising an expression vector, and said host cell may be a prokaryotic or a eukaryotic cell.

In another aspect, the present application discloses a method for producing said tumor-targeting peptide in the present application, including culturing said host cell for preparing said tumor-targeting peptide.

In another aspect, the present application discloses a pharmaceutical composition comprising a conjugate of the present application and a pharmaceutically acceptable carrier.

In some embodiments, the pharmaceutical composition comprises a radiotherapeutic agent, a radioactive nucleic acid, a toxin, a therapeutic agent, or a chemotherapeutic agent, or a combination thereof.

In another aspect, the present application discloses a pharmaceutical composition comprising a tumor-targeting peptide of the present application and a pharmaceutically acceptable carrier.

In another aspect, the present application discloses a method for treating a biological individual with a tumor comprising administering to said biological individual an effective amount of a conjugate of the present application; said tumor comprising cells expressing at least one EGFR family member.

In some embodiments, the tumor is one of breast cancer, colorectal cancer, pancreatic cancer, head and neck cancer, melanoma, ovarian cancer, prostate cancer, and non-small cell lung cancer.

In some embodiments, the method further comprises administering an effective dose of a therapeutic agent at the same time.

In some embodiments, the biological individual is a human.

In another aspect, the present application discloses a solution comprising an effective concentration of a conjugate disclosed thereof, said solution being a plasma of a biological individual.

The present application relates to a tumor-targeting peptide. The tumor-targeting peptide may be created by selecting and optimizing mutations in the amino acid sequence of S3-mimicking peptide (see below) and characterized by an improved binding specificity to EGFR. Said tumor targeting-peptide can be coupled with molecular imaging reagents (radioisotope labeling, fluorescence dye labeling, etc.) for its application in diagnostic analysis of tumor; or it can be coupled with therapeutic drugs for its application in targeted cancer therapy to reduce detrimental effects on normal cells and side effects to the patient while improving the efficacy of treatment; or it can be used as a competitor, with its high-affinity peptide structure, to directly compete and occupy the binding site of EGFRs, and to inhibit the growth of tumor cells as a way of treating cancer.

DETAILED DESCRIPTION

Figure 1:
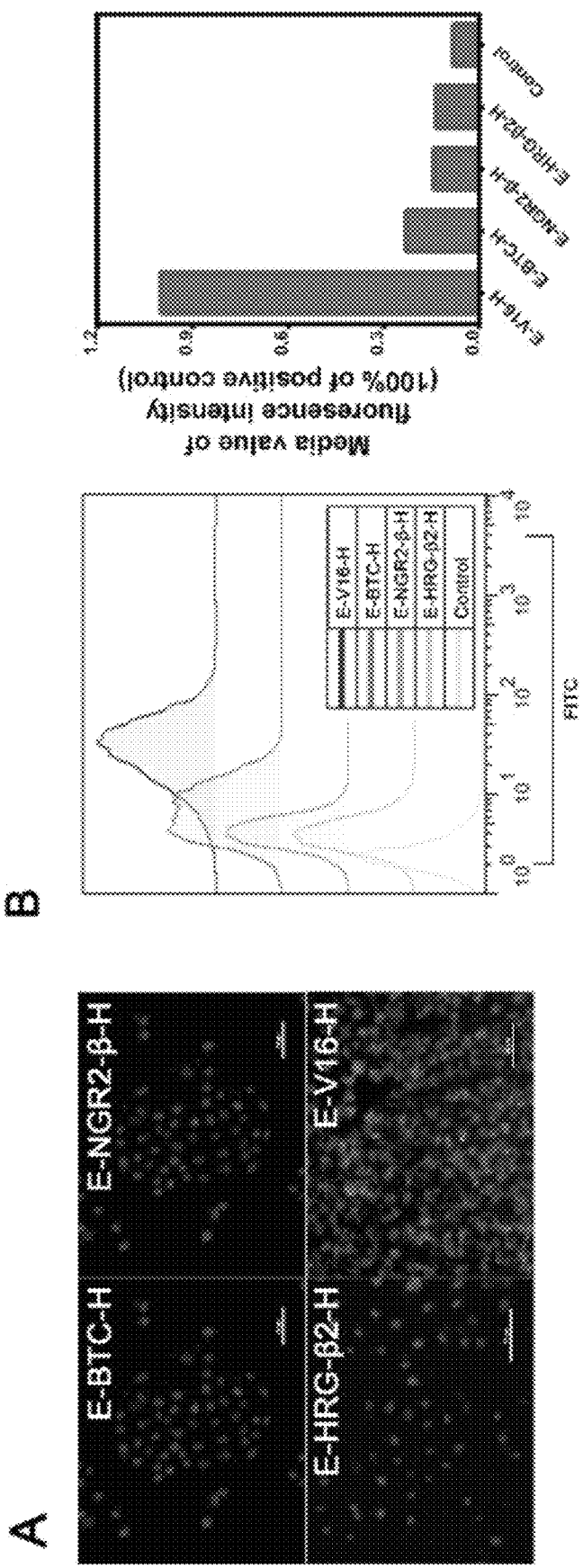
FIG. 1 shows a comparison of ELBD and other natural peptide sequences and their efficiencies as cell-penetrating peptides.

The application provides tumor-targeting peptides, cell-penetrating peptides, and their conjugates, compositions comprising the same, and methods of making and using the same. In one embodiment, the peptides, conjugates or compositions may be used for cancer treatment or diagnosis. Various techniques, methods and sequences disclosed in the Chinese Patent Application, CN 201310170530.6, which is incorporated herein in its entirety, may be used for this application.

The term "VGF third loop-like artificial peptide" (also known as "S3-mimicking peptide") refers to a group of short peptides capable of specifically binding to EGFRs, which may or may not exert the function of promoting cell growth and proliferation; whose structure complements with that of Domain III of the extracellular portion of EGFR; and which may or may not lead to dimerization of EGFRs. A representative of VGF third loop-like artificial peptides comprises two Cys residues and folds internally into a loop structure, which is similar to that of S3-mimeticking peptide and complements with Domain III when binds to EGFR, and is essential to exert its biological activity. Within this loop structure, these amino acid residues, Tyr, Gly, Arg, and the Leu at the C terminal are highly conserved, and a loss of any one of these conserved amino acids or a large deletion affects the Leu residue at the C terminal and can lead to a loss of its binding activity.

The term "tumor-targeting peptide" refers to a group of short peptide sequences, which are selected and optimized for artificial mutations in the amino acid sequence for EGFR-binding, S3-mimicking peptide and display the desired specificity for binding EFGR. Such peptides can be used for labeling, identifying, and diagnosing tumor cells, either by competitively binding to EGFR or by carrying cancer targeting drugs to the surface of tumor cells to exert targeted therapeutic effect.

In one embodiment, the tumor-targeting peptide may be coupled with molecular imaging reagents (radioisotope labeling, fluorescence dye labeling, etc.) for its application in diagnostic analysis of tumor. In one embodiment, the tumor-targeting peptide may be coupled with therapeutic drugs for its application in targeted cancer therapy by reducing detrimental effect on normal cells or side effect to patients and improving the efficacy of treatment. In one embodiment, because of its high affinity peptide structure, the tumor-targeting peptide may be used as a competitor to directly compete and occupy the binding site of EGFR, thereby treating cancer by inhibiting the growth of tumor cells.

Cell-penetrating peptides (CPPs), also known as protein translocation peptides or membrane translocation peptides, are a group of short peptides of 30 or fewer amino acids and are capable of penetrating cell membrane. Said CPPs include, but not limited to, trans-activating transcriptional activator (TAT) of human immunodeficiency virus (HIV), VP22 transcription factor of herpes simplex virus (HSV) type I, Penetratin derived from *Drosophila* Antennapedia Homeodomain (Antp), Transportan, those of human origin such as ARF, BagP, CytC, hCT, hLF, hClock, TCTP, NRTN, those of synthetic amphipathic peptides between the nuclear localization signal of large T antigen and various hydrophobic peptides such as MPF, MAP, and Pep-1, those of poly-arginine of varying lengths between 4 and 15 residues, SynB1, Polyomavirus Vpl, Bac, NF-KB, SV4OT antigen, HATF3, hCT, pVEC, Integrin, DPV6, S413PV, Poly-P, and one of heparin binding domains, of which the preferred CPPs include TAT (with an amino acid sequence, YGRKKRRRRRRR, SEQ ID NO. 21), or the carboxyl-terminal heparin binding domain of EC-SOD (with an amino acid sequence, GPGLWERQAREHSERKKRRRESECKAA, SEQ ID NO. 22), or a variant thereof, such as the CPPs described in Chinese Patent CN201210587097.1 and CN1049111. In one embodiment, the CPP may be HBEGF-derived HBEGF heparin binding domain, whose amino acid sequence is shown in SEQ ID NO.12.

A linker is a component of a protein that connects various structural and functional domains, which enables each domain to maintain its active conformation and exert its respective biological function. A linker peptide provides coordination, regulation, and transformation for the allosteric effect of each structural and functional domain, so as to prevent the protein from losing its biological activity due to the factors such as polarity and/or charges, spatial hindrance, and other factors. There are three forms of linkers: flexible, rigid, and cleavable. A linker peptide may exert its biological function depending on multiple forms of secondary structures, such as α-helix, beta sheet, coil/bend, and turn/loop. A linker in its native state often appears in the form of coil/bend, which is accounted for about 59% (Chen et al., Adv Drug Deliv Rev., Doi:10.1016/j.addr.2012.09.039). A linker peptide in the form of coil/bend has a certain degree of flexibility so that the two connected domains can be relatively free in their respective movement.

Tumor-targeting peptides are short peptides capable of exerting both cell penetrating activity via its CPP domain and tumor targeting activity as described.

Herein, said peptides, including but not limited to, tumor-targeting peptides, cell-penetrating peptides, tumor-targeting cell-penetrating peptides, and their derivatives, are subjected to modifications by using conventional methods available in the field. Such methods can modify either amino terminal or carboxyl terminal of a peptide, substitute any amino acid residue, or modify any side chain. For example, the methods for modifying terminals include N-terminal acetylation and C terminal amidation that protect amino group or carboxyl group, respectively. Fatty acids of different lengths may also be linked to the terminals of a peptide chain. PEG molecules can be glycosylated to increase their relative molecular weight as well as a steric hindrance, improve their stability to the polypeptide hydrolase, or prolong the retention time by the circulatory system in vivo. It is possible to extend or improve the half-life of peptide drugs by replacing individual amino acids that are prone to enzymatic cleavage, or by substituting L-amino acids with D-amino acids.

"Conjugate" refers to a group of short peptide conjugates, comprising said tumor-targeting peptide and an active moiety connected through a linker, wherein said active moiety may be a therapeutic agent, a diagnostic agent, a radioactive isotope, radionuclides, a toxin, or the combination of.

The peptides of the present application, including but not limited to, "tumor-targeting peptide," "cell-penetrating peptides," and "tumor-targeting cell-penetrating peptide," can be synthesized by using conventional liquid or solid phase synthesis methods. If a solid phase method is used for synthesis of said "tumor-targeting peptide", "tumor-targeting cell-penetrating peptide", a linker, such as 3-maleimide propionic acid N-hydroxysuccinimide ester, can be used to link said tumor-targeting cell-penetrating peptide to an anti-cancer drug, which includes but not limited to, doxorubicin, docetaxel, mitomycin, daunorubicin, carboplatin, camptothecin, hydroxycamptothecin, vincristine, bleomycin, 5-fluorouracil, phthalamide, gemcitabine, methotrexate, capecitabine, lomustine, topazide, capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-paclitaxel, or their derivatives or the combination of, in order to form conjugates that can be prepared as targeted anticancer drugs.

Using doxorubicin as an example, the specific procedure includes: dissolve doxorubicin and 3-maleimide propionic acid N-hydroxysuccinimide in dimethylformamide, respectively, add triethylamine to adjust pH, stir at room temperature for 2 h, pour into 50 ml ether, wash the precipitate with anhydrous ether twice, centrifuge to isolate and vacuum dry the precipitate; dissolve the precipitate and said tumor-targeting cell-penetrating peptide in the present application in dimethylformamide, add triethylamine, stir at room temperature for 2 h, pour into 10 ml ether, wash the precipitate with anhydrous ether twice, centrifuge to separate the precipitate, and vacuum dry the precipitate to obtain the desired conjugate.

The present application provides DNA sequences encoding said tumor-targeting peptides, tumor-targeting cell-penetrating peptides, and fusion proteins containing said peptides, as well as any vector and transformant containing the same.

The term "transformant" used herein refers to the host cell carrying heterologous DNA molecules.

The present application provides, by means of synthesis and recombinant techniques, methods for producing said "tumor-targeting peptides," tumor-targeting cell-penetrating peptides, or any fusion protein containing said peptides. Multiple nucleotide acids (DNA or RNA), vectors, transformants, and organisms can be isolated and purified by known methods in the field.

A vector may be, without limitation, a bacteriophage, plasmid, cosmid, micro chromosome, virus, or retroviral vector. A vector that can be used for cloning and/or expressing polynucleotides is a vector that is copied and/or expressed and can replicate and/or express polynucleotides in host cells. Polynucleotides and/or vectors may be used in any eukaryotic or prokaryotic cells, including mammalian cells (e.g. HeLa cells of human origin), monkey (e.g. Cos), rabbit (e.g. rabbit reticulocyte), rat and hamster (e.g. CHO, NSO and baby hamster kidney cells), or murine cells (e.g. L cells), plant cells, yeast, insect cells, or bacterial cells (e.g. E. coli). Examples of suitable vectors for various types of host cells are described in Current Protocols in Molecular Biology by Ausube et al., Greene Publishing Associates and Wiley-Interscience (1992) and Sambrook et al. (1989). The host cells containing these polynucleotides may be used to express a large quantity of proteins that can be used as drugs, diagnostic reagents, vaccines, and therapeutic agents.

A variety of methods have been developed to enable the ligation between polynucleotides and a vector through their complementary cohesive ends. For example, a DNA fragment with complementary sequences may be inserted into a region of a vector DNA. Then a recombinant DNA molecule is formed by ligating the complementary ends of the vector and the DNA fragment through hydrogen bonds.

A synthetic linker containing one or more restriction sites provides another example method for linking a DNA fragment and a vector. A DNA fragment that is prepared after being digested with DNA endonuclease may be treated with either T4 phage DNA polymerase or Escherichia coli DNA polymerase I, whose 3',5'-exonuclease activity can trim γ-single-stranded ends while DNA polymerase activity can fill in 3'-overhang ends. Therefore, a combination of these enzymatic activities produces a DNA segment with blunt ends. Then, in the presence of an enzyme capable of ligating blunt ends, such as T4 phage DNA ligase, DNA fragments with blunt ends may be incubated with an excessive molar ratio of synthetic linkers. Thus, the product of this reaction is a DNA segment with multiple cohesive sequences at its terminals. This DNA segment is subjected to digestion by appropriate restriction enzymes, followed by ligation with an expression vector previously prepared by digestion with said restriction enzymes for generating complementary cohesive ends to that of the DNA fragment. Synthetic linkers comprising a plurality of restriction endonuclease sites are commercially available.

A polynucleotide insert should become operational for expression when linked to a proper promoter compatible with the host cell, which may be a strong promoter and/or an inducible promoter. Examples of such promoters include bacteriophage λ PL promoter, E. coli lac, trP, phoA, and tac promoters, SV40 early and late promoters, and retroviral LTR promoter. There are other appropriate promoters known to any person of ordinary skill in this field. Furthermore, a recombinant expression vector comprises a transcription initiation site, a termination site, and within the region of transcription, a ribosome binding site for translation. The coding region of the transcript expressed by a DNA recombinant vector may begin with a translation initiation codon and end with a stop codon (UAA, UGA or UAG) from which a peptide is appropriately translated.

As mentioned above, the expression vector may include at least one selection marker. Such markers include dihydrofolate reductase, geneticin, glutamine synthase, or neomycin-resistant gene in eukaryotic cells, and tetracycline, kanamycin, or ampicillin-resistant gene in E. coli and other bacterial cultures. Representative examples of appropriate hosts include, but not limited to, bacterial cells, such as E. coli, Streptomyces, and Salmonella typhimurium cells; yeast cells, such as fungal cells (Saccharomyces cerevisiae or Pasteur Pichia pastoris); insert cells, such as Drosophila S2 and Spodoptera frugiperda SF9 cells; animal cells, such as CHO, COS, NSO 293, and Bowes melanoma cells; and plant cells. The appropriate medium and culture conditions for the host cells above are known in this field.

In order to effectively isolate and purify or secrete target proteins, protein tags are often used to facilitate protein separation and purification. Glutathione S-transferase (GST), hexa-histidine-tag peptide (His.Tag), protein A, and cellulose binding domain are commonly used. With the formation of a fusion protein between a specific protein tag and a target protein, the target protein may be isolated and purified by using the specific property of a protein tag. For example, His.Tag can specifically bind to Ni-chelating Sepharose column. To obtain a target protein, a protein tag may be removed from the purified fusion protein through digestion using a site-specific protease, such as Thrombin, Enteropeptidase, Factor Xa, or others.

The present application also comprises the host cells containing the nucleotide sequences of the present application, and said sequences can be linked to one or more heterologous control regions, such as promoters and/or enhancers, by using techniques known in the field. It is possible to select a strain of host cells capable of selectively regulating the expression of an inserted gene sequence, or modifying and processing the gene product in a desired manner. In the presence of certain inducers, the expression of some promoters increases, such that the expression of a genetically modified peptide can be regulated. In addition, different strains of host cells may have their characteristic and special mechanisms for protein translation, post-translational processing, and modification (such as phosphorylation, cleavage). Appropriate cell lines can be selected to ensure that the expressed foreign proteins are modified and processed in a desirable manner.

The nucleic acids and nucleic acid recombinant vectors of the present application can be introduced into host cells through transfection using calcium phosphate, DEAE-dextran, cationic lipid, electroporation, transduction, infection or other methods. These methods are described in a number of standard laboratory manuals, such as Basic Methods in Molecular Biology (1986) by Davis et al.

The DNA sequences that encode the fusion proteins of the present application may be linked to a vector consist of a selection marker for proliferation in host cells. In general, a plasmid vector can be introduced as a precipitant complex, such as a calcium phosphate precipitant or a cationic lipid complex. If the vector is a virus, it can be packaged into an appropriate packaging cell line in vitro and then transduced into host cells.

The successfully transformed cells, i.e., the cells harboring the DNA recombinant vector of the present application, can be identified by using well-known techniques. For example, culturing the cells containing a DNA recombinant vector can produce the desired peptide. The cells are collected and lysed by using the methods described in J. Mol. Biol. 1975, 98:503 by Southern, or in Biotech. 1985, 3:208 by Berent et al., to detect the target DNA in DNA fraction. Alternatively, antibodies may be used to detect the presence of proteins in the supernatant.

It is relatively convenient to recover and purify the fusion protein of the present application from cultured cells by using well-known methods, including ammonium sulfate or ethanol precipitation, acid extraction, anion or cation exchange chromatography, phosphate cellulose chromatography, hydrophobic interaction chromatography, affinity chromatography, hydroxyapatite chromatography, hydrophobic charge induction chromatography, and lectin chromatography. In some embodiments, high-performance liquid chromatography (HPLC) can be used for purification.

In some embodiments, the fusion protein of the present application may be purified using one or more of the above chromatography methods. In other embodiments, one or more column chromatography methods may be used to purify the fusion protein of the present application, including Q Sepharose FF column, SP Sepharose FF column, Q Sepharose High Performance Column, Blue Sepharose FF column, Blue Column, Phenyl Sepharose column, DEAE Sepharose, FF, Ni-Chelating Sepharose column, or Methyl column, and et al.

In one embodiment, the method that has been described in WO 00/44772, which is incorporated herein by reference in its entirety, may be used to purify the fusion protein of the present application. A technically skilled person in the field can easily modify certain aspects of said method and use it to purify the fusion protein of the present application. The fusion protein of the present application can be harvested from any recombinant prokaryotic or eukaryotic host, such as bacteria, yeast, plant, insect, and mammalian cells.

The conjugates of the present application can be used as active ingredients to treat various diseases caused by cell proliferation, such as tumors, including but not limited to: cancer of bone, including Ewing's sarcoma, osteosarcoma, chondrosarcoma; tumors of brain and CNS, including acoustic neuroma, neuroblastoma, glioma and other brain tumor, spinal cord tumors, breast cancer, colorectal cancer, advanced colorectal carcinoma; cancer of neuroendocrine, including: adrenocortical carcinoma, pancreatic carcinoma, pituitary cancer, thyroid cancer, lingual thyroid cancer, thymic carcinoma, multiple endocrine neoplasms; cancer of gastrointestinal system, including gastric cancer, esophageal cancer, small intestinal cancer, liver cancer, cholangiocarcinoma, gastrointestinal stromal tumor, gallbladder cancer; cancer of genitourinary, including testicular cancer, penile cancer, prostate cancer; gynecological cancer, including cervical cancer, ovarian cancer, vaginal cancer, uterine/endometrial cancer, perineum cancer, gestational trophoblastic tumor, carcinoma of fallopian tube, uterine sarcoma; head and neck cancer, including oral cancer, lip cancer, salivary gland cancer, laryngeal cancer, hypopharyngeal cancer, throat cancer, nasal sinus cancer, nasopharyngeal carcinoma; cancer of blood, including: childhood leukemia, acute lymphoblastic leukemia, acute myeloid leukemia, chronic lymphocytic leukemia, chronic myelogenous leukemia, hairy cell leukemia, acute promyelocytic leukemia, plasma cell leukemia; cancer of bone marrow and blood disorders, including bone marrow dysplasia syndrome, myeloproliferative disorders, aplastic anemia, Fanconi anemia, idiopathic macroglobulinemia; cancer of lung, including small cell lung cancer, non-small cell lung cancer; cancer of lymph nodes, including Hodgkin's disease, non-Hodgkin's lymphoma, cutaneous T-cell lymphoma, peripheral T-cell lymphoma, AIDS associated lymphoma; cancer of eye, including: retinoblastoma, uveal melanoma; skin cancer, including melanoma and non-melanoma skin cancer, Merkel cell carcinoma; soft tissue sarcoma, for example: children soft tissue sarcoma, adult soft tissue sarcoma, Kaposhi sarcoma; cancer of urinary system, including renal cell carcinoma, Wilms tumor, bladder cancer, urinary tract cancer or metastatic carcinoma.

The fusion protein disclosed in the present application can be used for treating cancer, primarily cervical cancer, breast cancer, colorectal cancer, bladder cancer or lung cancer.

The preferred types of tumors that can be treated by using the fusion protein of the present application are solid tumors and hematologic malignancies.

Herein, the term "tumor" refers to a wide range of disorders characterized by uncontrolled abnormal growth of cells.

The effective dosage of said active ingredient may vary with the drug delivery mode and the severity of the treated disease. For most large mammals, the total dose of said active ingredient is about 0.01-1000 mg/day. In general, the range of clinical doses for adults is 0.01-200 mg/day, preferably, 0.05-100 mg/day.

"Effective dose" or "treatment volume" refers to the sufficient amount for curative effect. An effective dose may be delivered as single-dose or multiple-dose. In general, an effective dose is sufficient to mitigate, improve, stabilize, slow down, or delay the further development of the disease.

The present application provides compositions for treating cancers. In one embodiment, the composition contains the fusion protein disclosed thereof. When the composition of the present application is used for said treatment, the fusion protein may be mixed with one or more pharmaceutically acceptable carrier or excipient to formulate a dosage of different administration routes, such as tablets, capsules, powder, granules, syrup, solution, oral liquid, spirit agent, tincture, aerosol, powder spray, injection, sterile powder for injection, suppository, and so on.

"Pharmaceutical acceptable" ingredients are substances that apply to people and/or animals without excessive adverse effects (such as toxicity, irritation, and allergy), and that have a reasonable benefit/risk ratio. A "pharmaceutical acceptable carrier" is a solvent, suspension, or excipient used to transmit the fusion protein disclosed thereof to an animal or a person for pharmaceutical or food acceptability. The carrier can be liquid or solid.

The fusion protein disclosed thereof can be administered orally, intravenously, intramuscularly, or subcutaneously.

The dosage forms that can be administered orally include tablet, capsule, powder, granule, syrup, solution, and spirit agent. Solid-state carriers include starch, lactose, calcium hydrogen phosphate, microcrystalline cellulose, sucrose, white clay, silica gel, talcum powder, low substituted hydroxypropyl cellulose, sodium carboxymethyl starch, polyethylene pyrrolidone. Liquid carriers include sterile water, ethanol, polyethylene glycol, nonionic surfactants and edible oils (e.g. corn oil, peanut oil, and sesame seed). Adjuvants commonly used in the preparation of pharmaceutical compositions include flavorings, colorants, preservatives (such as hydroxy phenyl alkyl butyl ester, sodium benzoate, sorbic acid), and antioxidants (such as vitamin E, vitamin C, pyrosulfite sulfate and dibutylhydroxytoluene).

The dosage forms that can be used for injectable formulations include injections, sterile powder for injection, which are mixtures of one or more pharmaceutical acceptable excipients. Solvents include sterile water, ethanol, glycerin, propylene glycol, and polyethylene glycol. In addition, it is necessary to add antibacterial agents (such as benzyl alcohol, hydroxyphenylbutyl ester, and thiomersal), isotonic modulators (such as sodium chloride and glucose), suspending agent (such as sodium carboxymethyl cellulose and methyl cellulose), emulsifiers (such as Tween 80 and lecithin), antioxidant (such as vitamin E, vitamin C, and pyrosulfite sulfate), and filler (such as lactose and mannitol).

From the standpoint of a feasible drug preparation and administration, the preferred pharmaceutical composition may be solid compositions, in particular, lyophilized powder for injection. The preferred delivery method is intravenous administration.

The followings are detailed examples of the present application. It should be understood that these examples are merely illustration and are not intended to limit the scope of the present application. An experimental method that does not specify any specific conditions in the following examples is usually in accordance with conventional conditions, or in accordance with conditions recommended by manufacturer. The proportions and percentages are based on weight unless otherwise stated.

Herein, a peptide sequence of SEQ ID NO. 1, or abbreviated as ELBD or V16, represents the same peptide.

Example 1: Construction of Expression Vectors

A. Construction of EGFP-Tn-CPP Expression Vectors
(1) Construction of EGFP-Tn-HBD Mutant Expression Vector In the China Patent Application No. 201310170530.6, we disclosed one type of tumor cell-targeting and cell-penetrating peptides characterized by its cell-penetrating activity via the CPP structural domain and its tumor cell-targeting activity via the VGF third loop-like artificial domain. To obtain higher efficacy in cell-penetrating and tumor-targeting, a series of nucleotide sequences, which are flanked by BamHI and SalI restriction sites and encode mutant peptides of S3 structural analogue based on their structural and mutational needs, were synthesized using DNA artificial solid-phase synthesis, of which the peptide sequences, SEQ ID NO. 1-11, are listed in Table I.

TABLE 1

The synthetic sequence of VGF third loop and the amino acid sequences of selected mutant peptides.

| Name | Sequence | SEQ ID |
|---|---|---|
| VGF | RCSHGYTGIRCQHVVL | [[\]] SEQ ID NO. 16 |
| S3 | RCSHGYTGIRCQAWL | [[\]] SEQ ID NO. 17 |
| V16 | RCSHYTGIRCSHMAATTAGIYTGIRCQHVVL | SEQ ID NO. 1 |
| V16-1 | RASHYTGIRCSHMAATTAGIYTGIRCQHWL | SEQ ID NO. 2 |
| V16-2 | RCSHYTGIRASHMAATTAGIYTGIRCQHVVL | SEQ ID NO. 3 |
| V16-3 | RCSHYTGIRCSHMAATTAGIYTGIRGQHVVL | SEQ ID NO. 4 |
| V16-4 | RCSHYTGIRCSEAAAKEAGIYTGIRCQHWL | SEQ ID NO. 5 |
| V16-5 | RCSHYTGIRCSGGGGSGAGIYTGIRCQHWL | SEQ ID NO. 6 |
| V16-6 | RCSHMAATTAGIYTGIRCQHVVL | SEQ ID NO. 7 |
| V16-7 | RCSHYTGIRCSHMAATTAGIYTGIRCQH | SEQ ID NO. 8 |
| V16-8 | RCSHYTGIRCSHGIYTGIRCQHVVL | SEQ ID NO. 9 |
| V16-9 | YTGIRCSHMAATTAGIYTGIRCQHVVL | SEQ ID NO. 10 |
| V16-10 | RCSHYTGIRCSHGAAAAAGIYTGIRCQHVVL | SEQ ID NO. 11 |
| CPP | KRKKKGKGLGKKRDPCLRKYK | SEQ ID NO. 12 |
| | RCSHYTGIRCSHMAATTAGIYTGIRCQHVVLVDGGKRKKKGKGLGKKRDPCLRKYK | SEQ ID NO. 13 |
| | RCSHYTGIRCSHMAATTAGIYTGIRCQHVDGGKRKKGKGLGKKRDPCLRKYK | SEQ ID NO. 14 |

TABLE 1-continued

The synthetic sequence of VGF third loop and the amino acid sequences of selected mutant peptides.

| Name | Sequence | SEQ ID |
|---|---|---|
| | RCSHYTGIRC SHGIYTGIRC QHVVLVDGGK RKKKG KGLGKKRDPC LRKYK | SEQ ID NO. 15 |
| VGF | RCSHGYTGIR CQHVVL | SEQ ID NO. 16 |
| S3 | RCSHGYTGIR CQAWL | SEQ ID NO. 17 |
| Sense primer | 5'-CGCGGAT CCGGTGGTGG TGGTTCTGGT GGTGGTGGT T-3' | SEQ ID NO. 18 |
| Antisense primer | 5'-CGCCTCG AGGTCTTTAC CTTT-3' | SEQ ID NO. 19 |
| Linker | HMAATT | SEQ ID NO. 20 |
| TAT | YGRKKRRRRR RR | SEQ ID NO. 21 |
| HBD | GPGLWERQAR EHSERKKRRR ESECKAA | SEQ ID NO. 22 |
| | YXGXR | SEQ ID NO. 23 |
| Optimized ELBD | RCSHYTGIRC SHGIYTGIRC QH | SEQ ID NO. 24 |
| | YTGIRCSH | SEQ ID NO. 25 |

Starting from the EGFP-T0-HBD expression plasmid (see China Patent Application No.: CN 201310170530.6, ESH in Example 1), the original EGFP-T0-HBD-pET28a expression vector was digested with both BamHI and SalI restriction enzymes, and ligated with the synthetic DNA fragments by using T4 DNA ligase.

After transformed into *E. coli* DH5a strain, the recombinant plasmid DNA was recovered from the culture and was subjected to sequence validation, such that the construction of a series of EGFP-Tn-HBD-pET28a expression vectors, where n=1-11, was completed. For V16 that has been specially named ELBD, the corresponding expression vector is now known as EGFP-ELBD-HBD-pET28a.

At the same time, other vectors expressing the third loop sequence of other native growth factors, EGFP-BTC-HBD-pET28a, EGFP-NRG2-β-HBD-pET28a, and EGFP-HRG-β2-HBD-pET28a, were constructed.

(2) Construction of a Vector Series Expressing EGFP-Tn-TAT Mutants

The nucleotide sequences, that encode the cell-penetrating peptide TAT and are flanked by SalI and XhoI restriction sites, were synthesized by using DNA artificial solid phase synthesis method and were insert into the EGFP-Tn-HBD-pET28a expression vector series that have been previously harvested and digested with SalI+XhoI restriction enzymes in Example 1, such that this series of EGFP-Tn-TAT-pET28a expression vectors that express the cell-penetrating peptide TAT were constructed.

(3) Construction of the EGFP-ELBD-H2 Expression Vector

Using the EGFP-ELBD-HBD-pET28a plasmid as a vector, the DNA sequence, encoding H2 cell-penetrating peptide and flanked by SalI and XhoI restriction sites, was optimized for *E. coli* codons and was synthesized by using DNA artificial solid phase method, where H2 is another type of cell-penetrating peptides originated from human heparin-like growth factor. The EGFP-Tn-HBD-pET28a expression vector was digested with SalI and XhoI, and was ligated with said DNA fragment by using T4 DNA ligase.

After transformed into *E. coli* DH5a strain and incubated overnight at 37° C. for 15 h, the recombinant plasmid DNA was purified by using DNA recovery kit and was submitted to a DNA sequencing company for sequence verification.

(4) Construction of EGFP-TAT Expression Vector

The DNA sequence, encoding TAT penetrating peptide and flanked by BamHI and XhoI restriction sites, was optimized for *E. coli* codons and was synthesized by using DNA artificial solid-phase synthesis method. This synthetic DNA fragment was inserted into the EGFP-ELBD-HBD-pET28a expression vector previously digested with BamHI and XhoI restriction enzymes, and was followed by transformation into *E. coli* DH5a strain and incubation at 37° C. overnight. A plasmid DNA recovery kit was used to purify the recombinant plasmid DNA, which was submitted to a DNA sequencing company for sequence verification.

B. Construction of Vectors Expressing Recombinants of Different Antitumor Protein Drugs and ELBD-CPP (1) Construction of TCS-ELBD-H2 Expression Vector The DNA primers whose sequences contain both BamHI and XhoI restriction sites were synthesized by using DNA artificial solid phase synthesis method, the PCR amplification was carried out using the ELBD-H2 gene of the EGFP-ELBD-H2-pET28a plasmid as a template, thereby both BamHI and XhoI restriction sites were added.

Use the EGFP-ELBD-H2-pET28a plasmid DNA as a template, the PCR amplification was carried out using the sense and antisense primers whose sequences are derived from that of ELBD-H2 gene as shown below, as well as those of BamHI and XhoI restriction sites, respectively:

Sense primer 1:
(SEQ ID NO. 18)
5'-CGCGGATCCGGTGGTGGTG

GTTCTGGTGGTGGTGGTT-3'

Antisense primer 2:
(SEQ ID NO. 19)
5'-CGCCTCGAGGTCTTTACCTTT-3'

The PCR amplification reaction condition includes: 5-min of denaturating at 95° C.; 33 cycles of 45 sec of denaturating at 95° C., 30 sec of annealing at 58° C., and 30 sec of elongation at 72° C.; and 10 min of final extension at 72° C.

The amplified product was purified by using a DNA fragment recovery kit, followed by BamHI and XhoI restriction digestion and DNA recovery. At the same time, the TCS-HBD-pET28b plasmid vector was digested with BamHI and XhoI restriction enzymes, and the plasmid fragment was recovered. T4 DNA ligase was used for ligation. After transformed into *E. coli* DH5a strain and incubated at 37° C. for 15 h overnight, a plasmid DNA recovery kit was used to purify the recombinant plasmid DNA, which was submitted to a DNA sequencing company for sequence verification.

(2) Construction of MAP30-ELBD-H2 Expression Vector

The steps are similar to those for constructing the TCS-ELBD-H2 expression vector above, and so were the primers and PCR amplification reaction conditions.

The primers containing BamHI and XhoI restriction sites were synthesized, and the ELBD-H2 gene in the original plasmid of EGFP-ELBD-H2-pET28a was used as a template for the PCR amplification, such that BamHI and XhoI restriction sites were added to the amplified fragment.

The amplified fragment was purified using a DNA fragment recovery kit, followed by BamHI and XhoI restriction digestion and DNA recovery. At the same time, the MAP30-HBD-pET28b plasmid vector was digested with BamHI and XhoI, and the plasmid fragment was recovered. T4 DNA ligase was used for ligation. After transformed into E. coli DH5a strain and incubated at 37° C. for 15 h overnight, a plasmid DNA recovery kit was used to purify the recombinant plasmid DNA, which was submitted to a DNA sequencing company for sequence verification.

Example 2: Expression and Purification of Recombinant Protein

A. Expression and Purification of EGFP Recombinant Protein Series (1) Expression and Purification of EGFP-Tn-HBD Recombinant Protein Series ① The construction scheme of the EGFP-Tn-HBD-pET28a plasmid is described in Example 1. A single colony of the EGFP-Tn-HBD-pET28a plasmid transformed bacteria was picked from a solid LB medium plate of the preserved strain, and cultured in 30 ml of LB liquid medium containing kanamycin (10-50 mg/L) in a 37° C. shaker until its OD600 was about 0.5-1.0.

② The culture medium containing kanamycin (10-50 mg/L) was inoculated with this bacterium culture at 1% of its volume and cultured for expansion until its OD600 was about 0.5-1.0.

③ The culture temperature was adjusted to a range between 15° C. and 20° C., a proper amount of IPTG (0.1-10 mM) was add to induce the expression of target protein in culture for continuous 10-20 h, and then the bacteria were harvested using a 500-1000 rpm low-speed centrifuge.

④ The bacteria were suspended in 20 mM Tris-HCl buffer (pH 8.0-8.5), sonicated at certain sonication power (10-100 w). After high speed centrifugation at low temperature (4-10° C.), the supernatant was discarded and the inclusion body was retained.

⑤ The inclusion body was washed with 1.0-0.5% of Triton for 10-60 min.

⑥ The inclusion body was denatured for 5-30 min using 6 M-8 M of urea.

⑦ The inclusion body was renatured through dialysis, by gradually reducing the concentration of urea to 0 M.

Following the steps above, both EGFP-Tn-HBD recombinant protein and EGFP-ELBD-TAT recombinant protein can be expressed and purified, respectively.

(2) Expression and Purification of EGFP-ELBD-H2 Recombinant Protein

① The construction scheme of EGFP-ELBD-H2-pET28a plasmid is described in Example 1. A single colony of EGFP-ELBD-H2-pET28a transformed bacteria was picked from a solid LB medium plate of the preserved strain and cultured in 30 ml LB liquid medium containing kanamycin (10-50 mg/L) in a 37° C. shaker until OD600 was about 0.5-1.0.

② The culture medium containing kanamycin (10-50 mg/L) was inoculated with this bacterium culture at 1% of its volume and cultured for expansion until its OD600 was about 0.5-1.0.

③ The culture temperature was adjusted to a range between 15° C. and 20° C., a proper amount of IPTG (0.1-10 mM) was add to induce the expression of target protein in culture for continuous 10-20 h, and then the bacteria were harvested using a 500-1000 rpm low-speed centrifuge.

④ The bacteria were suspended in 20 mM Tris-HCl buffer (pH 8.0-8.5), sonicated at certain sonication power (10-100 w). After high speed centrifugation (8000-13400 rpm) at low temperature (4-10° C.), the supernatant containing the target protein was retained.

⑤ The collected supernatant was separated by affinity chromatography with nickel chelate affinity column. Similar to most methods of nickel chelate affinity chromatography for purifying target protein, different concentrations of imidazole elution in gradient (20 mM imidazole elution, 200 mM imidazole elution) were used to wash and collect the target protein in the elution corresponding to different concentrations of imidazole.

(3) Expression and Purification of EGFP-TAT Recombinant Protein

① The construction scheme of the EGFP-TAT-pET28a plasmid is described in Example 1. A single colony of EGFP-TAT-pET28a transformed bacteria was picked from a solid LB medium plate of the preserved strain and cultured in 30 ml LB liquid medium containing kanamycin (10-50 mg/L) in a 37° C. shaker until OD600 was about 0.5-1.0.

② The culture medium containing kanamycin (10-50 mg/L) was inoculated with this bacterium culture at 1% of its volume and cultured for expansion until its OD600 was about 0.5-1.0.

③ The culture temperature was adjusted to a range between 15° C. and 20° C., a proper amount of IPTG (0.1-10 mM) was add to induce the expression of target protein in culture for continuous 10-20 h, and then the bacteria were harvested using a 500-1000 rpm low-speed centrifuge.

④ The bacteria were suspended in 20 mM Tris-HCl buffer (pH 8.0-8.5) and sonicated at certain sonication power (10-100 w). After high speed centrifugation at low temperature (4-10° C.), the supernatant containing the target protein was retained.

⑤ The collected supernatant was separated by affinity chromatography with nickel chelate affinity column. Similar to most methods of nickel chelate affinity chromatography for purifying target protein, different concentrations of imidazole elution in gradient (10 mM imidazole elution, 200 mM imidazole elution, and 1 M imidazole elution) were used to wash and collect the target protein in the elution corresponding to different concentrations of imidazole.

(4) Expression and Purification of EGFP-ELBD-TAT Recombinant Protein

① The construction scheme of the EGFP-ELBD-TAT-pET28a plasmid is described in Example 1. A single colony of EGFP-ELBD-TAT-pET28a transformed bacteria was picked from a solid LB medium plate of the preserved strain and cultured in 30 ml LB liquid medium containing kanamycin (10-50 mg/L) in a 37° C. shaker until OD600 was about 0.5-1.0.

② The culture medium containing kanamycin (10-50 mg/L) was inoculated with this bacterium culture at 1% of its volume and cultured for expansion until its OD600 was about 0.5-1.0.

③ The culture temperature was adjusted to a range between 15° C. and 20° C., a proper amount of IPTG (0.1-10 mM) was add to induce the expression of target protein in culture for continuous 10-20 h, and then the bacteria were harvested by low-speed centrifugation at 500-1000 rpm.

④ The bacteria were suspended in 20 mM Tris-HCl buffer (pH 8.0-8.5) and sonicated at certain sonication power (10-100 w). After high speed centrifugation at low temperature (4-10° C.), the supernatant containing the target protein was retained.

⑤ The collected supernatant was separated by affinity chromatography with nickel chelate affinity column. Similar to most methods of nickel chelate affinity chromatography for purifying target protein, different concentrations of imidazole elution in gradient (10 mM imidazole elution, 200 mM imidazole elution, and 1 M imidazole elution) were used to wash and collect the target protein in the elution corresponding to different concentrations of imidazole.

B. Expression and Purification of Recombinant Proteins of Different Antitumor Proteins and ELBD-CPP (1) Expression and Purification of TCS-ELBD-H2 Recombinant Protein ① The construction scheme of the TCS-ELBD-H2-pET28b plasmid is described in Example 1. A single colony of TCS-ELBD-H2-pET28a transformed bacteria was picked from a solid LB medium plate of the preserved strain and cultured in 30 ml LB liquid medium containing kanamycin (10-50 mg/L) in a 37° C. shaker until OD600 was about 0.5-1.0.

② The culture medium containing kanamycin (10-50 mg/L) was inoculated with this bacterium culture at 1% of its volume and cultured for expansion until its OD600 was about 0.5-1.0.

③ The culture temperature was adjusted to a range between 15° C. and 20° C., a proper amount of IPTG (0.1-10 mM) was add to induce the expression of target protein in culture for continuous 10-20 h, and then the bacteria were harvested by low-speed centrifugation at 500-1000 rpm.

④ The bacteria were suspended in 20 mM Tris-HCl buffer (pH 8.0-8.5) and sonicated at certain sonication power (10-100 w). After high speed centrifugation at low temperature (4-10° C.), the supernatant containing the target protein was retained.

⑤ The collected supernatant was separated by affinity chromatography with nickel chelate affinity column. Similar to most methods of nickel chelate affinity chromatography for purifying target protein, different concentrations of imidazole elution in gradient (20 mM imidazole elution, 50 mM imidazole elution, and 200 mM imidazole elution) were used to wash and collect the target protein in the elution corresponding to different concentrations of imidazole.

(2) Expression and Purification of MAP30-ELBD-H2 Recombinant Protein

① The construction scheme of MAP30-ELBD-H2-pET28b plasmid is described in Example 1. A single colony of MAP30-ELBD-H2-pET28b transformed bacteria was picked from a solid LB medium plate of the preserved strain and cultured in 30 ml LB liquid medium containing kanamycin (10-50 mg/L) in a 37° C. shaker until OD600 was about 0.5-1.0.

② The culture medium containing kanamycin (10-50 mg/L) was inoculated with this bacterium culture at 1% of its volume and cultured for expansion until its OD600 was about 0.5-1.0.

③ The culture temperature was adjusted to a range between 15° C. and 20° C., a proper amount of IPTG (0.1-10 mM) was add to induce the expression of target protein in culture for continuous 10-20 h, and then the bacteria were harvested by low-speed centrifugation at 500-1000 rpm.

④ The bacteria were suspended in 20 mM Tris-HCl buffer (pH 8.0-8.5) and sonicated at certain sonication power (10-100 w). After high speed centrifugation at low temperature (4-10° C.), the supernatant containing the target protein was retained.

⑤ The collected supernatant was separated by affinity chromatography with nickel chelate affinity column. Similar to most methods of nickel chelate affinity chromatography for purifying target protein, different concentrations of imidazole elution in gradient (20 mM imidazole elution, 50 mM imidazole elution, and 200 mM imidazole elution) were used to wash and collect the target protein in the elution corresponding to different concentrations of imidazole.

Example 3: Study of the Efficiency of Mutant Cell-Penetrating Peptides

A. Comparison of the Efficiency of Mutant Cell-Penetrating Peptides:

(1) Analysis of the Cell-Penetrating Effect of EGFP-Tn Recombinant Protein Comprising the Cell-Penetrating Peptide HBD At 2 μM of concentration, the recombinant protein samples were incubated with tumor cells for 12 h in an in vitro culture, the cell-penetrating effect of various EGFP-Tn-HBD recombinant proteins on human breast cancer cells, Bcap, was analyzed and compared by flow cytometry. The recombinant proteins comprising natural growth factor-derived third loop sequences (EGFP-BTC-HBD, EGFP-NRG2-β-HBD, EGFP-HRG-β2-HBD) were compared to various recombinant mutant samples at 2 μm sample concentration and at the same time after incubated with human breast cancer cells, Bcap, in an in vitro culture, for their cell-penetrating effects analyzed and characterized by the laser confocal technique.

The results showed that the cell-penetrating effect of EGFP-ELBD-HBD on Bcap cells was significantly better than that of the recombinant proteins comprising other natural growth factor-derived third loop sequences (EGFP-BTC-HBD, EGFP-NRG2-β-HBD, EGFP-HRG-β2-HBD). FIG. 1, A shows the result of laser confocal analysis; B shows the result of flow cytometry, where EGFP-ELBD-HBD is labeled as E-V16-H, EGFP-BTC-HBD is labeled as E-BTC-H, EGFP-NRG2-β-HBD is labeled as E-NRG2-β-H, and EGFP-HRG-β2-HBD is labeled as E-HRG-β2-H.

Figure 2:
FIG. 2 shows a comparison of the cell-penetrating efficiency of ELBD and mutant fusion proteins.

Taken together the sequences in Table 1 and the efficiency of cell-penetrating from both laser confocal and flow cytometry experiments (FIG. 2), it becomes clear that the position and number of Cys in a putative loop have a definitive effect on the cell-penetrating result. The cell-penetrating efficiency of V16-9, V16-3, V16-2, and V16-1 was lower than that of ELBD (V16). As compared to V16-3 and V16-2, the effect of V16-1 was worse and comparable to that of V16-9. This implies that these three Cys have important effects on the tertiary structure of the mutants, all of which may participate in the formation of the loop structure and exert certain effect on the cell-penetrating efficiency. Using the computer simulation program from Zhang Lab, an analysis of ELBD's spatial structure indicates that, of all simulated structures, only C2-C10 and C2-C26, but not C10-C26, exist, suggests that C2 has higher probability to participate in the process of loop formation. And only the C2-participated loop formation is more similar to the native third loop structure, which contains the highly conserved amino acid residues (Y-X-G-X-R, SEQ ID NO.23) in the loop.

Compared to ELBD (V16), V16-6 (SEQ ID NO.7) lacks the sequence of YTGIRCSH (SEQ ID NO.25) and its cell-penetrating efficiency is greatly affected, which indicates the import role of the N-terminal sequence of ELBD (V16) in maintaining its high efficiency of synergistic cell-penetrating effect. It is also possible that loss of the second Cys in the absence of this sequence affects the spatial structure of the domain as well as the loop formation. This is because the computer simulation analysis shows that a loop structure is unlikely formed between the second and third Cys, and that one possible scenario is the presence of sequences for a putative α-helix structure near the two Cys, which makes it difficult to form disulfide bonds between the two Cys.

The results of V16-10, V16-4 and V16-5 indicate that an insertion in the middle of a potential loop-forming structure may directly affect the size and shape of the loop, as well as the spatial orientation of those conservative amino acid residues, Y-X-G-X-R (SEQ ID NO.23), which may decrease the cell-penetrating efficiency. Although previous studies have confirmed that Leu47 in the C-terminal region of EGF plays an important role in the binding of EGF to EGFR, the result of our mutational analysis shows that the removal of the VVL sequence did not affect the cell-penetrating effect of V16-8 mutant. This implies that the flexible C-terminal tail of ELBD-H structures may not participate in the process of receptor binding, and that the Cys residue that affects the domain structure and the Y-X-G-X-R sequence (SEQ ID NO.23) for direct binding to the receptor are the key factors. The α-helix sequence inserted in the middle of the loop may ensure the optimal orientation of the Y-X-G-X-R sequence (SEQ ID NO.23) on both sides, so that it can efficiently recognize and bind to the ErbB receptor. In this context, we believe that the ELBD sequence can be optimized to RCSHYTGIRCSHGIYTGIRCQH (SEQ ID NO.24).

(2) The Concentration and Time Dependence of Mutant Cell-Penetrating Peptides

Figure 3:
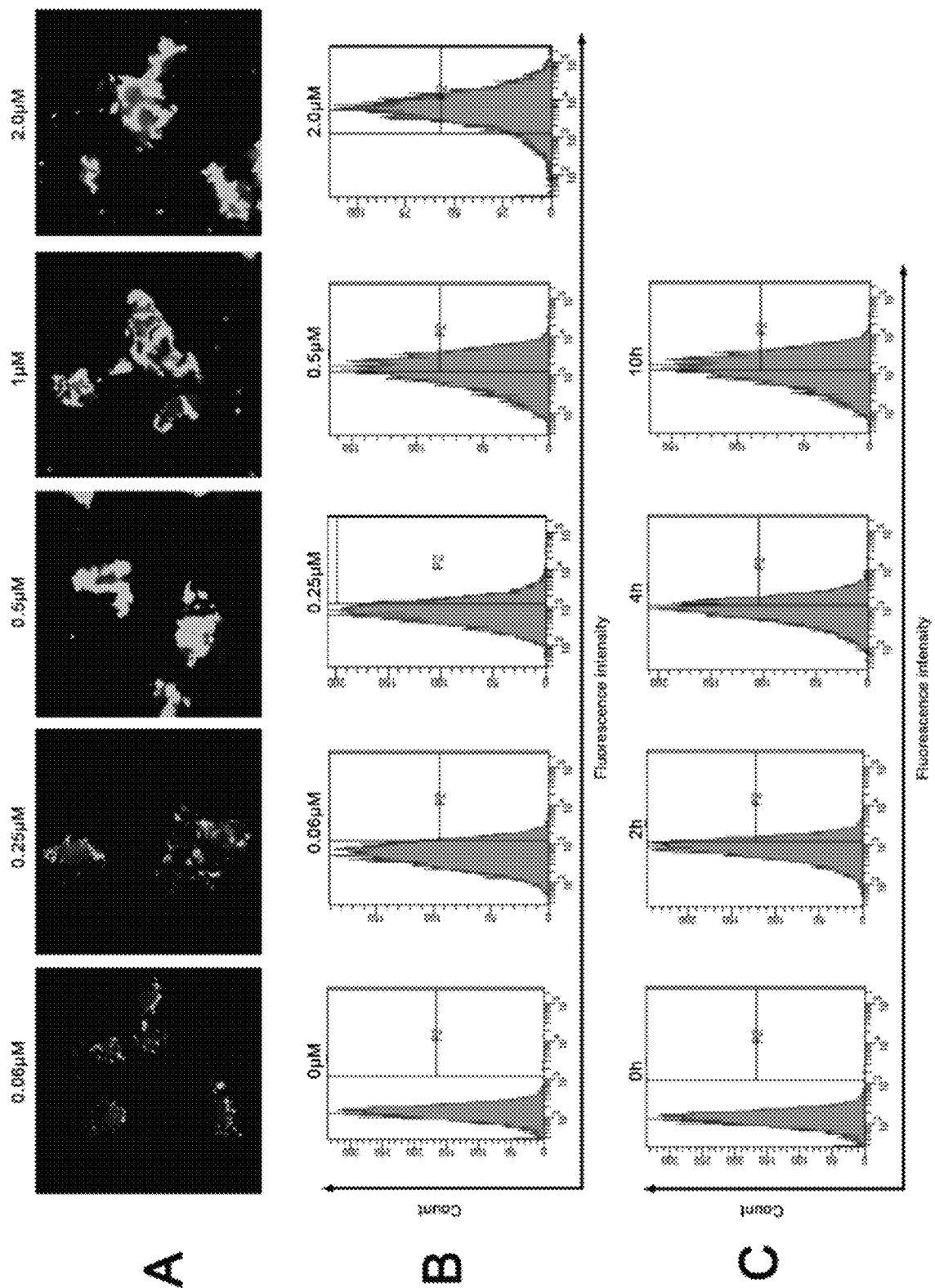
FIG. 3 shows the concentration and time-dependency as a function of cell-penetrating efficiency for EGFP-ELBD-HBD recombinant protein.

The gradient of protein concentrations and the duration of incubation time (0-12 h) were studied by using EGFP-ELBD-HBD recombinant protein in different concentrations (0-2 µM). The experimental results show that, with prolonged incubation time and increased concentration of the recombinant protein, the cell-penetrating efficiency of the recombinant protein EGFP-ELBD-HBD on human breast cancer cells, Bcap, was significantly increased. The finding indicates that the cell-penetrating efficiency of the recombinant protein is both time dependent and concentration dependent (FIGS. 3A and 3B indicates the concentration dependence, and 3C indicates the time dependence).

B. Broad-Spectrum Analysis of Tumor-Targeting Peptide ELBD:

In order to examine its universality as a tumor-targeting peptide and its broad-spectrum of applications in combination with cell-penetrating peptides, we fused the sequence of ELBD with that of HBD (a cell-penetrating peptide derived from human EC-SOD heparin binding domain, Chinese Patent ZL200810044084.3), TAT (a HIV-derived cell-penetrating peptide), HBP (heparin binding region of heparin-like growth factor, a human cell-penetrating peptide), and various other cell-penetrating peptides (referred to as CPPs) to produce samples of recombinant proteins: 30 µM of EGFP-TAT, 2 µM E-ELBD-TAT, 30 µM of EGFP-HBD, and 2 µM of EGFP-ELBD-HBD, which were then incubated with Bcap cells for 12 h, respectively, and the efficiency as a cell-penetrating peptide was determined by flow cytometry.

Figure 4:
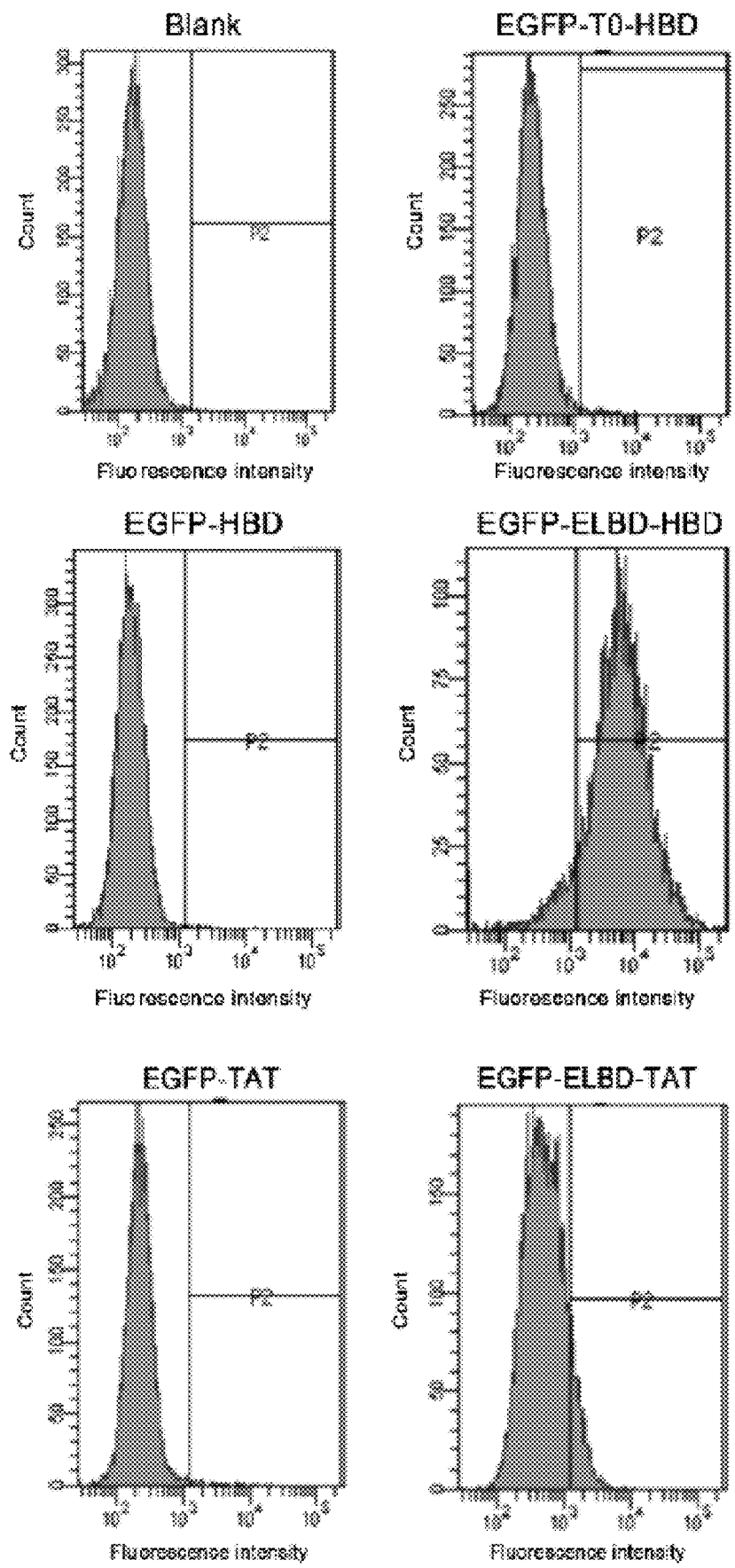
FIG. 4 shows the broad spectrum of ELBD peptide.

As a result, it was confirmed that the ELBD sequence as a tumor-targeting peptide can greatly improve not only the cell-penetrating efficiency of HBD but also that of the classic cell-penetrating peptide TAT, and HBP as well. The result demonstrates that ELBD can synergistically enhance the tumor-targeting and cell-penetrating effects of different types and sources of CPP, and to a large extent, the ELBD sequence can improve the cell-penetrating efficiency of various sources and sequences of cell-penetrating peptides (FIG. 4).

C. Cell Selectivity of EGFP-ELBD-HBD Recombinant Protein

Eleven types of cells were used to study the EGFP-ELB-HBD recombinant protein for its characteristics on tumor-targeting. They included 9 types of human tumor cells: HeLa (human cervical cancer cells), Bcap (human breast cancer cells), A549 (human lung cancer cells), A357 (human malignant melanoma), T24 (human bladder cancer cells), MGC-803 (human gastric cancer cells), 95D (human giant cell lung cancer cells), BxPC-3 (human pancreatic cancer cells), and 5637 (human bladder cancer cells); and 2 types of normal somatic cells: MRC-5 (human embryonic lung fibroblasts), and 293T (human renal epithelial cells).

Figure 5:
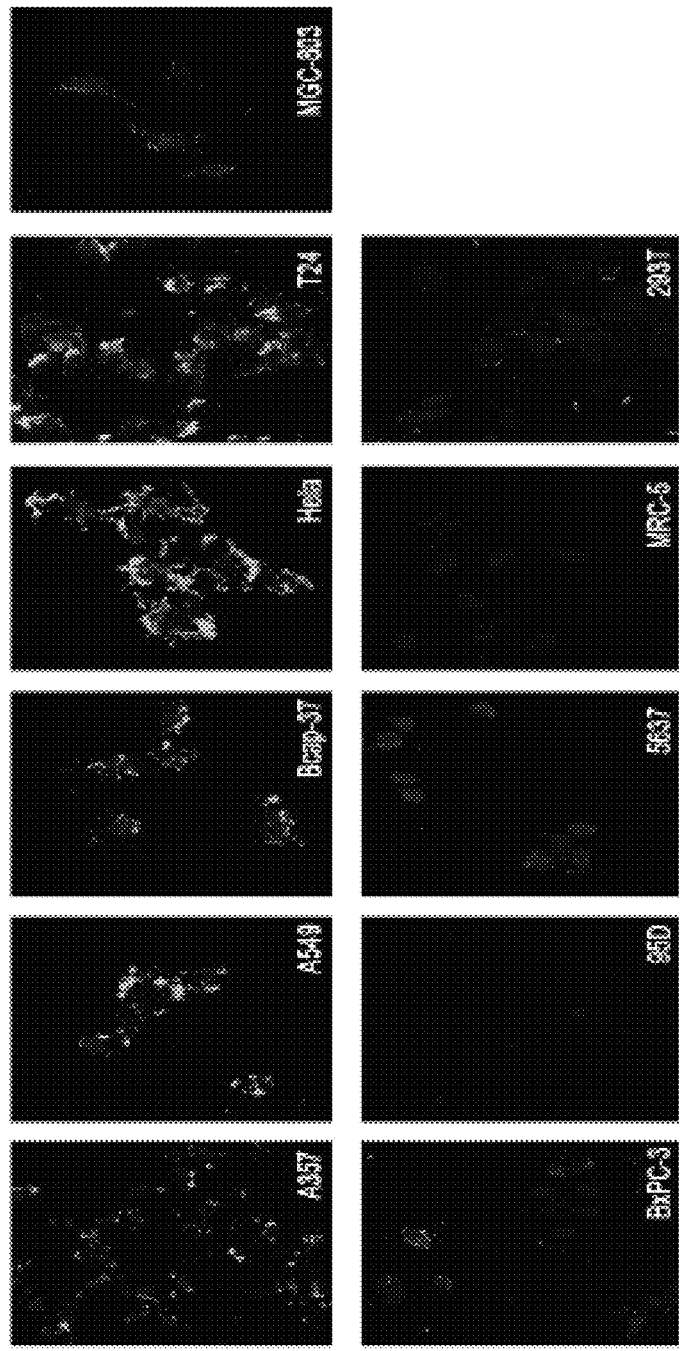
FIG. 5 shows the selective affinity of the EGFP-ELBD-HBD recombinant protein to human cells.
Figure 5:
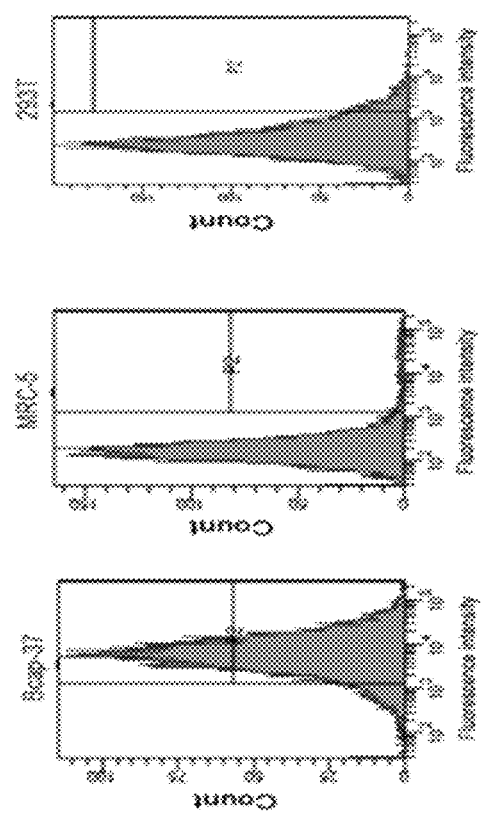

The concentration of the recombinant protein was set at 1 µM, and the incubation time was 12 h. The result shows that the EGFP-ELBD-HBD recombinant protein had little cell-penetrating effect on two normal cells, MRC-5 and 293T; while displayed different degrees of cell-penetrating effect on cancer cells: HeLa, Bcap, A549, T24, and A357 (FIG. 5). This phenomenon may be due to the different distribution of a target receptor on the surface of different cancer cells, leading to the seemly different cell-penetrating capacities of the EGFP-ELBD-HBD recombinant protein to different tumor cells. However, to the normal cells, the number of membrane receptors, such as epidermal growth factor receptor or EGFR, are much lower than cancer cells, this characteristic difference in cell selectivity is key to ELBD as a tumor-targeting peptide.

Example 4: Analysis of the Surface Binding Ability of Mutants to Tumor Cells by ELISA ELISA was used to determine the binding ability of both EGFP-S3-HBD (China Patent Application No. CN 201310170530.6) and EGFP-ELBD-HBD recombinant proteins to the surface receptors of human cervical cancer HeLa cells.

The human cervical cancer cells were seeded in a 96-well cell culture plate at the density of $1 \times 10^3$-$1 \times 10^5$ cells/well (sufficient to cover a 96-well plate in 24 h), cultured at 37° C. for 24 h, and washed with PBS for 15 min for 3 times. Cold glutaraldehyde at 4° C. and 0.1-0.25% of concentration was added into each well at 50 µl/well to fix the cells at 4° C. for 10-45 min; the fixed cells were washed with PBS for 15 min for 3 times, and covered with 1% BSA/PBS solution at 200 µl/well at 4° C. overnight; the plate was washed with PBST buffer (PBS with 0.05% of TWEEN-20) 3 times, each time for 15 min; the recombinant fusion protein in a series of dilutions was added to the 96-well plate at 50 µl/well, each dilution had triplicated in 3 wells in parallel, and the plate was incubated at 37° C. for 2 h; after washed with PBST for 3 times, a murine monoclonal antibody against His-Tag was added (1:1000-1:3000 dilution) at 50 μl/well, and the plate was incubated at 37° C. for 2 h; after washed with PBST for 3 times, a horseradish peroxidase labeled sheep anti-rat IgG secondary antibody (1:800-1:2500 dilution) was added at 50 μl/well, and the plate was incubated at 37° C. for 2 h; after washed with PBST for 5 times, TMB substrate solution was added at 100-200 μl/well, and the plate was incubated at room temperature and in dark to avoid light reaction for 10-30 min. The reaction was stopped by adding 50 μl of 2 mol/L sulfate per well, and the absorbance value at 450 nm was immediately determined on a microplate reader.

Figure 6:
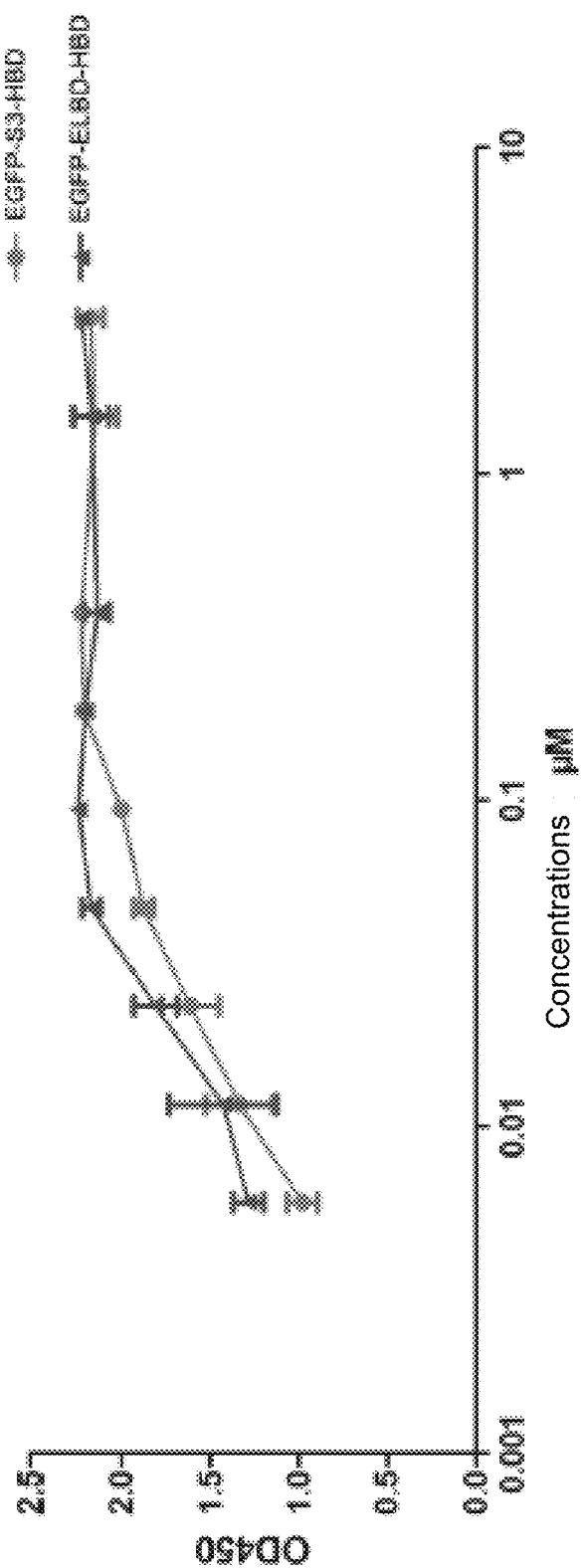
FIG. 6 shows the affinity of EGFP-S3-HBD and EGFP-ELBD-HBD to the surface of HeLa cells, respectively.

As shown in FIG. 6, ELBD can bind to the surface receptors of HeLa cells at lower concentrations, suggesting that it is much easier for ELBD to bind to the surface of cancer cells, which in turn makes it easier to further improve the cell-penetrating efficacy of recombinant proteins.

Example 5: ELBD-CPP Tumor-Targeting and Cell-Penetrating Peptide Improves the Pharmacological Effect of Protein Drugs TCS is a protein drug derived from plant stem tubers (*Trichosanthes kirilowii* Maxim.), which exhibits antitumor activity and the activity of ribosome inactivating protein (RIP), and is capable of inhibiting protein synthesis in the in vitro cell free system.

Figure 7:
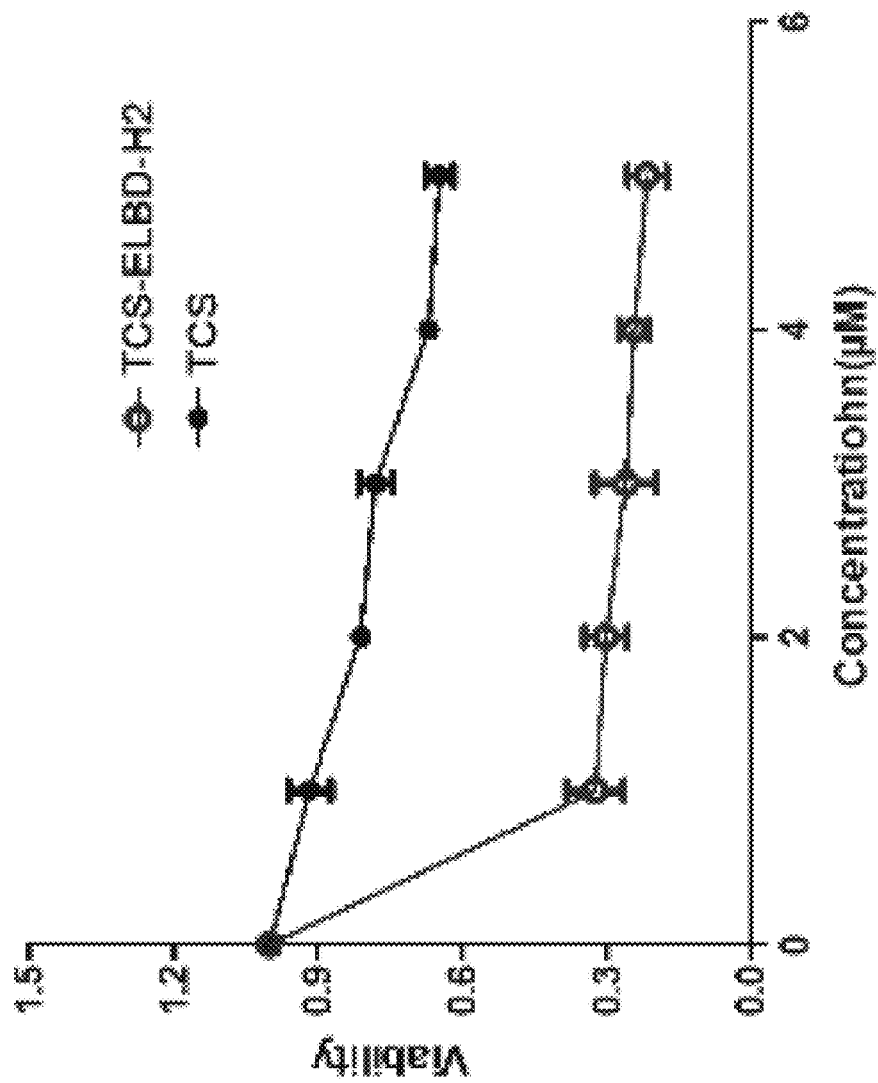
FIG. 7 shows the inhibitory effect of TCS-ELBD-CPP recombinant protein on tumor cell proliferation.

When the TCS gene sequence is fused with the ELBD mutant sequence and H2 cell-penetrating peptide sequence and is expressed as a fusion protein, TCS-ELBD-H2, its inhibition on B16 (rat melanoma cells) was significantly increased (FIG. 7).

Figure 8:
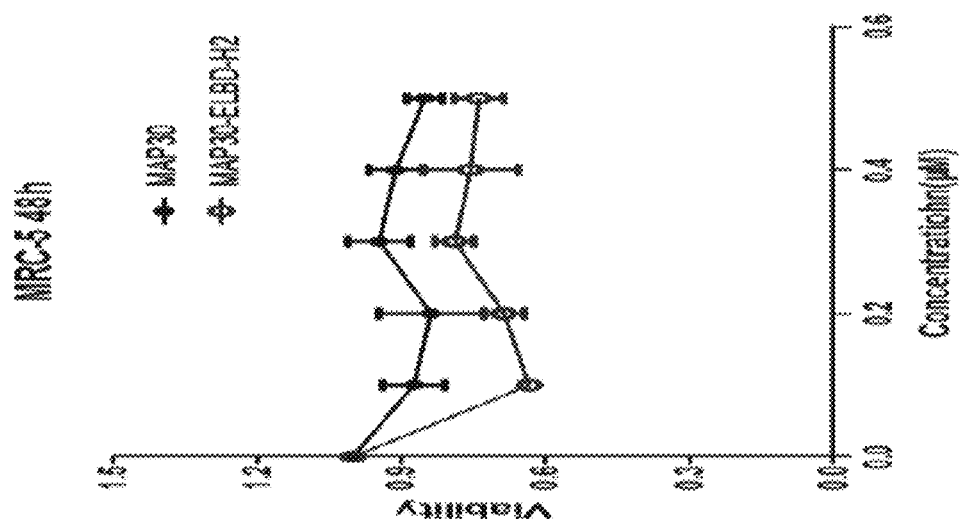
FIG. 8 shows the inhibitory effect of MAP30-ELBD-CPP recombinant protein on normal and tumor cells, respectively.
Figure 8:
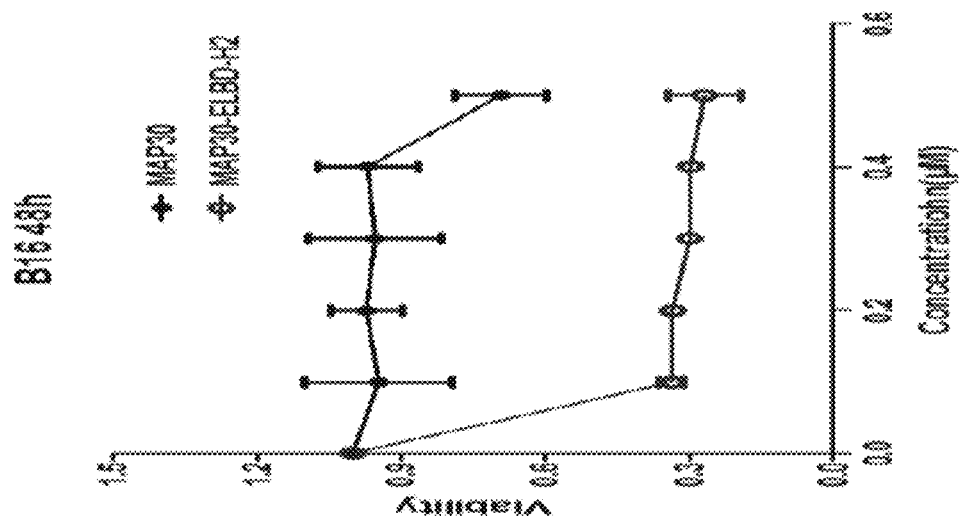
Figure 8:
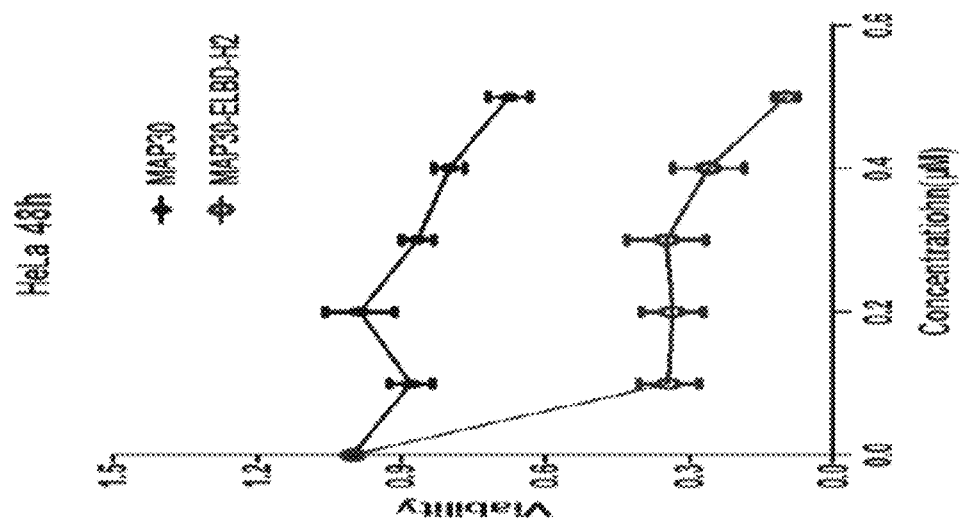

MAP30 is also a protein drug with antitumor activity, which comes from balsam pear seeds (*Momordica charantia* L.) but is also a kind of RIP protein. When expressed as a ELBD-H2 fusion protein, MAP30-ELBD-H2, its inhibition on tumor cells HeLa and B16 cells was significantly increased, while its inhibition on the normal cell MRC-5 was not significantly changed (FIG. 8).

The scope of the present application is not limited by any specific example, any example is intended only as a single example of various aspects of the present application, and also, the scope includes methods and compositions of functional equivalence. In practice, various modifications will be readily apparent to those skilled in the art in view of the foregoing description and drawings. The improvement also falls within the scope of the appended claims. Each of the references mentioned above is hereby incorporated by the reference in its entirety.

What is claimed is:

1. A tumor-targeting peptide, comprising, a first component comprising an amino acid sequence YXGXR (SEQ ID NO: 23) and a second component comprising independently an amino acid sequence YXGXR (SEQ ID NO: 23), wherein the first component is coupled to the second component through a linker component, wherein Y comprises a tyrosine or its derivative, G comprises a glycine or its derivative, R comprises an arginine or its derivative, and X comprises a naturally occurring-amino acid selected from an amino acid having a side chain comprising an aliphatic group or a hydroxyl-containing group.

2. The tumor-targeting peptide of claim 1, wherein the linker component comprises an amino acid sequence configured to form an alpha-helix structure.

3. The tumor-targeting peptide of claim 1, wherein the linker component comprises a rigid alpha-helix structure.

4. The tumor-targeting peptide of claim 1, wherein the linker component comprises an amino acid sequence HMAATI (SEQ ID NO: 20).

5. The tumor-targeting peptide of claim 1, wherein the linker component consists of one amino acids residue.

6. The tumor-targeting peptide of claim 5, wherein the linker component consists of histidine or its derivative.

7. The tumor-targeting peptide according to claim 1, wherein said tumor-targeting peptide comprises a peptide having an amino acid sequence selected from SEQ ID NO: 1-4, 8, or 9.

8. The tumor-targeting peptide according to claim 1, wherein the tumor-targeting peptide has a binding specificity to a member of epidermal growth factor receptor (EGFR) family.

9. A conjugate, comprising the tumor-targeting peptide of claim 1 and an active moiety, wherein the tumor-targeting peptide is conjugated to an active moiety through a linker;
wherein the tumor-targeting peptide has a binding specificity to a member of epidermal growth factor receptor (EGFR) family;
and
wherein the active moiety comprises a therapeutic agent, a diagnostic agent, a radioisotope, a radionuclide, a toxin, or a combination thereof.

10. The conjugate of claim 9, wherein the therapeutic agent comprises a cell-penetrating peptide (CCP).

11. The conjugate of claim 10, wherein the cell-penetrating peptide is selected from SEQ ID NO. 12, an amino acid sequence derived from a transactivator of transcription (TAT), an amino acid sequence derived from a heparin-binding domain (HBD) of HBEGF-derived HBEGF, or a derivative thereof.

12. The conjugate of claim 10, wherein the conjugate comprises a peptide having an amino acid sequence selected from SEQ ID NOS: 13 to 15.

13. The conjugate of claim 9, wherein the therapeutic agent comprises a radio-therapeutic agent, a chemotherapeutic agent, an antibody, an enzyme, or a combination thereof.

14. The conjugate of claim 9, wherein the diagnostic agent comprises a radio-diagnostic agent, a fluorescent agent, a quantum dot, or a combination thereof.

15. A pharmaceutical composition, comprising the conjugate of claim 9 and a pharmaceutically acceptable carrier.

16. The pharmaceutical composition of claim 15, further comprising radioisotope, radionuclide, a toxin, a therapeutic agent, a chemotherapeutic agent or a combination thereof.

17. A method of treating a subject with a cancer, comprising administering to the subject an effective amount of the conjugate of claim 9, wherein the cancer comprises cells expressing at least one member of the EGFR family.

18. The method of claim 17, further comprising co-administering an effective amount of a therapeutic agent.

19. A pharmaceutical composition, comprising the tumor-targeting peptide of claim 1 and a pharmaceutically acceptable carrier.

* * * * *